(12) United States Patent
Straussman et al.

(10) Patent No.: US 11,920,162 B2
(45) Date of Patent: Mar. 5, 2024

(54) EX-VIVO CULTURE SYSTEM AND METHODS OF USING SAME

(71) Applicant: Yeda Research and Development Co. Ltd., Rehovot (IL)

(72) Inventors: Ravid Straussman, Mazkeret Batia (IL); Nancy Gavert, Rehovot (IL)

(73) Assignee: Yeda Research and Development Co. Ltd., Rehovot (IL)

(*) Notice: Subject to any disclaimer, the term of this patent is extended or adjusted under 35 U.S.C. 154(b) by 436 days.

(21) Appl. No.: 16/499,333

(22) PCT Filed: Apr. 3, 2018

(86) PCT No.: PCT/IL2018/050390
§ 371 (c)(1),
(2) Date: Sep. 30, 2019

(87) PCT Pub. No.: WO2018/185760
PCT Pub. Date: Oct. 11, 2018

(65) Prior Publication Data
US 2020/0224171 A1    Jul. 16, 2020

Related U.S. Application Data

(60) Provisional application No. 62/481,738, filed on Apr. 5, 2017.

(51) Int. Cl.
| | |
|---|---|
| *A61K 9/20* | (2006.01) |
| *A61K 31/138* | (2006.01) |
| *A61K 31/337* | (2006.01) |
| *A61K 31/439* | (2006.01) |
| *A61K 31/4545* | (2006.01) |
| *A61K 31/4748* | (2006.01) |
| *A61K 31/502* | (2006.01) |
| *A61K 31/513* | (2006.01) |
| *A61K 31/519* | (2006.01) |
| *A61K 31/5377* | (2006.01) |
| *A61K 31/675* | (2006.01) |
| *A61K 31/704* | (2006.01) |
| *A61K 31/7068* | (2006.01) |
| *A61K 33/243* | (2019.01) |
| *A61L 27/26* | (2006.01) |
| *A61L 27/54* | (2006.01) |
| *A61L 27/58* | (2006.01) |
| *A61P 35/00* | (2006.01) |

(Continued)

(52) U.S. Cl.
CPC .......... *C12N 5/0693* (2013.01); *A61K 31/138* (2013.01); *A61K 31/337* (2013.01); *A61K 31/439* (2013.01); *A61K 31/4545* (2013.01); *A61K 31/4748* (2013.01); *A61K 31/502* (2013.01); *A61K 31/513* (2013.01); *A61K 31/519* (2013.01); *A61K 31/5377* (2013.01); *A61K 31/675* (2013.01); *A61K 31/704* (2013.01); *A61K 31/7068* (2013.01); *A61K 33/243* (2019.01); *A61P 35/00* (2018.01); *C12M 25/00* (2013.01); *G01N 33/5011* (2013.01); *C12N 2503/02* (2013.01); *C12N 2503/04* (2013.01); *C12N 2513/00* (2013.01)

(58) Field of Classification Search
CPC .............. C12N 5/0693; C12N 2503/02; C12N 2503/04; C12N 2513/00; C12N 2500/02; C12N 2533/40; C12N 2533/76; C12N 2539/00; A61K 31/138; A61K 31/337; A61K 31/439; A61K 31/4545; A61K 31/4748; A61K 31/502; A61K 31/513; A61K 31/519; A61K 31/5377; A61K 31/675; A61K 31/704; A61K 31/7068; A61K 33/243; A61P 35/00; C12M 25/00; G01N 33/5011; G01N 33/5082; G01N 33/5026

See application file for complete search history.

(56) References Cited

U.S. PATENT DOCUMENTS

| | | |
|---|---|---|
| 2005/0130254 A1 | 6/2005 | Park |
| 2010/0203575 A1 | 8/2010 | Peschanski et al. |

(Continued)

FOREIGN PATENT DOCUMENTS

| | | |
|---|---|---|
| JP | 2014-505675 | 3/2014 |
| JP | 61-058582 | 6/2022 |

(Continued)

OTHER PUBLICATIONS

Naipal et al., BMC Cancer (2016) 16:78. (Year: 2016).*
Meijer et al. Future Sci. OA (Mar. 2017) 3(2), FSO190 (Year: 2017).*
Toutain et al. Cell Biology and Toxicology. 1998; 14: 175-190 (Year: 1998).*
Vickers et al. Chemico-Biological Interactions 150 (2004) 87-96 (Year: 2004).*
Morimoto et al. Human Reproduction vol. 22, No. 12 pp. 3170-3177, 2007. (Year: 2007).*

(Continued)

*Primary Examiner* — Mina Haghighatian
*Assistant Examiner* — Janice Y Silverman
(74) *Attorney, Agent, or Firm* — Foley Hoag LLP; Brendan T. Jones

(57) ABSTRACT

Ex-vivo culture systems are provided. Accordingly there is provided a culture system comprising a culture medium and a precision-cut tissue slice placed on a tissue culture insert, wherein the precision-cut tissue slice is maintained in a highly oxygenated atmosphere containing at least 50% oxygen and wherein said culture is rotationally agitated facilitating intermittent submersion of the tissue slice in the culture medium. Also provided are methods of culturing a tissue and methods of using the culture system for selecting a drug for the treatment of a disease.

21 Claims, 10 Drawing Sheets
(10 of 10 Drawing Sheet(s) Filed in Color)

(51) Int. Cl.
C12M 1/12 (2006.01)
C12N 5/0775 (2010.01)
C12N 5/09 (2010.01)
G01N 33/50 (2006.01)

(56) References Cited

U.S. PATENT DOCUMENTS

2014/0228246 A1 8/2014 Sundaram et al.
2014/0302491 A1 10/2014 Nadauld et al.

FOREIGN PATENT DOCUMENTS

| WO | WO 2002/044344 | 6/2002 |
| WO | WO 2009/034108 | 3/2009 |
| WO | WO 2012/083260 | 6/2012 |
| WO | WO 2018/185760 | 10/2018 |

OTHER PUBLICATIONS

Hung et al. Proceedings of the Society for Experimental Biology and Medicine 122.1 (1966): 121-126. (Year: 1966).*
Monteil et al. BMC Cancer (2016) 16:78. (Year: 2016).*
Zimmerman et al. Cytotechnology (2009) 61:145-152. (Year: 2009).*
Vickers et al. Toxicological Sciences 82, 534-544 (2004). (Year: 2004).*
Obatomi et al. Toxicology in Vitro 12 (1998) 725-737 (Year: 1998).*
Request for Examination and Search Report dated Jul. 15, 2021 From the (Rospatent), Federal Government Institution of Industrial Property of the Federal Service of Intellectual Property, Patents and Trademark of the Russian Federation Re. Application No. 2019134857 and Its Translation Into English. (10 Pages).
Andreeva "Russian Dissertation (PhD-thesis) of Natalia Andreeva from Lomonosov Moscow State University", 121P., 2016.
Verkhovskaya et al. "The Effect of Glycerol Alcoxy-Deratives on Morphological and Functional Properties of ContinuousCell Culture", Problemy Kriobiologii,1,:30-33, 1990. with English Abstract.
International Preliminary Report on Patentability dated Oct. 17, 2019 From the International Bureau of WIPO Re. Application No. PCT/IL2018/050390. (19 Pages).
International Search Report and the Written Opinion dated Jul. 9, 2018 From the International Searching Authority Re. Application No. PCT/IL2018/050390. (16 Pages).
De Graaf et al. "Preparation and Incubation of Precision-Cut Liver and Intestinal Slices for Application in Drug Metabolism and Toxicity Studies", Nature Protocols, 5(9): 1540-1551, Published Online Aug. 19, 2010.
De Kanter et al. "Precision-Cut Organ Slices as a Tool to Study Toxicity and Metabolism of Xenobiotics With Special Reference to Non-Hepatic Tissues", Current Drug Metabolism, 3(1): 39-59, Feb. 2002.
Gerlach et al. "Slice Cultures From Head and Neck Squamous Cell Carcinoma: A Novel Test System for Drug Susceptibility and Mechanisms of Resistance", British Journal of Cancer, XP055252040, 110(2): 479-488, Published Online Nov. 21, 2013. p. 480-483.
Grinshpun et al. "Ex Vivo Organ Culture as Potential Prioritization Tool for Breast Cancer Targeted Therapy", Cancer Biology & Therapy, XP002781948, 19(8): 645-648, Published Online Apr. 13, 2018. p. 2, Left col. Last Full Para.
Grosso et al. "Breast Cancer Tissue Slices as a Model for Evaluation of Response to Rapamycin", Cell and Tissue Research, 352(3): 671-684, Published Online May 1, 2013.
Koch et al. "Murine Precision-Cut Liver Slices (PCLS): A new Tool for Studying Tumor Microenvironments and Cell Signaling Ex Vivo", Cell Communication and Signaling, 12(73): 1-14, Published Online Nov. 7, 2014.

Majumder et al. "Predicting Clinical Response to Anticancer Drugs Using an Ex Vivo Platform That Captures Tumour Heterogeneity", Nature Communications, 6(6169): 1-14, Published Online Feb. 27, 2015.
Maund et al. "Optimization and Comprehensive Characterization of a Faithful Tissue Culture Model of the Benign and Malignant Human Prostate", Laboratory Investigation, 94(2): 208-221, Feb. 2014.
Meijer et al. "Ex Vivo Tumor Culture Systems for Functional Drug Testing and Therapy Response Prediction", Future Science, XP002781946, 3(2): 1-13, Published Online Mar. 27, 2017. Para 'Organotypic Tumor Tissue Slices', p. 5-9, Table 1.
Meijer et al. "Nutlin-3 Preferentially Sensitises Wild-Type P53-Expressing Cancer Cells to DR5-Selective TRAIL Over RhTRAIL", British Journal of Cancer, 109(10): 2685-2695, Published Online Oct. 17, 2013.
Merz et al. "Organotypic Slice Cultures of Human Gliobalstoma Reveal Different Susceptibilities to Treatment", Neuro-Oncology, XP002781947, 15(6): 670-681, Advance Access Publication Apr. 10, 2013. p. 671-673.
Naipal et al. "Tumor Slice Culture System to Assess Drug Response of Primary Breast Cancer", BMC Cancer, XP055296179, 16(1): 78-1-78-13, Published Online Feb. 9, 2016. Abstract, p. 2-4.
Parajuli et al. "Precision-Cut Slice Cultures of Tumors From MMTV-Neu Mice for the Study of the Ex Vivo Response to Cytokines and Cytotoxic Drugs", In Vitro Cellular & Developmental Biology—Animal, 45(8): 442-450, Published Online Jun. 16, 2009.
Roife et al. "Ex Vivo Testing of Patient-Derived Xenografts Mirrors the Clinical Outcome of Patients With Pancreatic Ductal Adenocarcinoma", Clinical Cancer Research, 22(24): 6021-6030, Dec. 15, 2016.
Stoff-Khalili et al. "Preclinical Evaluation of Transcriptional Targeting Strategies for Carcinoma of the Breast in a Tissue Slice Model System", Breast Cancer Research, 7(6): R1141-R1152, Published Online Nov. 16, 2005.
Vaira et al. "Preclinical Model of Organotypic Culture for Pharmacodynamic Profiling of Human Tumors", Proc. Natl. Acad. Sci. USA, PNAS, 107(18): May 4, 2010.
Vickers et al. "Organ Slice Viability Extended for Pathway Characterization: An In Vitro Model to Investigate Fibrosis", Toxicological Sciences, 82(2): 534-544, Published Online Sep. 29, 2004.
Zimmermann et al. "Improved Reproducibility in Preparing Precision-Cut Liver Tissue Slices", Cytotechnology, 61(3): 145-152, Published Online Dec. 20, 2009.
Notice of Reasons for Refusal dated Jan. 5, 2022 From the Japan Patent Office Re. Application No. 2019-554559. (4 Pages).
Translation dated Jan. 20, 2022 of Notice of Reasons for Refusal dated Jan. 5, 2022 From the Japan Patent Office Re. Application No. 2019-554559. (4 Pages).
Notice of Reasons for Refusal dated Jul. 19, 2022 From the Japan Patent Office Re. Application No. 2019-554559. (4 Pages).
Translation dated Jul. 29, 2022 of Notice of Reasons for Refusal dated Jul. 19, 2022 From the Japan Patent Office Re. Application No. 2019-554559. (4 Pages).
Gavert et al. "Ex vivo organotypic cultures for synergistic therapy prioritization identify patient-specific responses to combined MEK and Src inhibition in colorectal cancer", Nature Cancer, vol. 3, pp. 219-231 (2022).
Davies et al., "Capturing complex tumour biology in vitro: histological and molecular characterisation of precision cut slices", *Scientific reports* 5(1): 17187 (2015).
Hanks et al., "A clinical trial of cResponse, a functional assay for cancer precision medicine." *Presented at American Association for Cancer Research Conferenc* (2023).
Golan et al.,"A clinical evaluation of an ex vivo organ culture system to predict patient response to cancer therapy" Frontiers in Medicine, 10,1221484 (2023).
Szalowska et al., "Effect of oxygen concentration and selected protocol factors on viability and gene expression of mouse liver slices" Toxicology in Vitro, vol. 27, pp. 1513-1524 (2013).

* cited by examiner

Adapting Core Biopsies to EVOC

Three cores are extracted from tissue and placed beside one anther in liquid agarose Agarose cooled and piece with embedded cores removed "en bloc"

Block re-embedded in agarose and cut with vibrotome to 270μM thickness

After PFA fixation and FFPE preparation Sample cut and stained with H&E

EX-VIVO CULTURE SYSTEM AND METHODS OF USING SAME

RELATED APPLICATIONS

This application is a National Phase of PCT Patent Application No. PCT/IL2018/050390 having International filing date of Apr. 3, 2018, which claims the benefit of priority under 35 USC § 119(e) of U.S. Provisional Patent Application No. 62/481,738 filed on Apr. 5, 2017. The contents of the above applications are all incorporated by reference as if fully set forth herein in their entirety.

FIELD AND BACKGROUND OF THE INVENTION

The present invention, in some embodiments thereof, relates to an ex-vivo culture system and methods of using same.

Conventional selection of anti-cancer therapeutic regimes is primarily based on the cancer tissue of origin, the stage and grade of the tumor and the overall health of the patient. Such treatment regimes are effective in some of the patients, however they are toxic, inducing many adverse effects which may be life threatening.

The availability of targeted drug therapies and the possibility of identifying patient specific tumor markers has instructed personalized treatment options but simultaneously requires extensive use of genetic profiling [see e.g. Dancey et al. (2012) *Cell* 148, 409-420; and Garraway et al. (2013) *J. Clin. Oncol. Off. J. Am. Soc. Clin. Oncol.* 31, 1806-1814]. However, the extrapolation of genetic data to specific treatment regimes is complex, and predicting patient response is unreliable. For example, in the case where a patient's tumor is characterized by more than one targetable mutation, it is very difficult to predict which of the potential drugs will be most effective. The same is true when there is more than one drug available for a specific mutation. Choosing therapy is thus heavily dependent upon trial and error.

Various technologies are available to directly test the response of a patient's cancer cells to a specific treatment, such as tumor derived cell lines generated from patient tumors and patient-derived xenograft (PDX) models [see e.g. Crystal et al. (2014) *Science* 346, 1480-1486; Clevers et al. (2016) *Cell* 165, 1586-1597; and Hidalgo et al. (2014) *Cancer Discov.* 4, 998-1013]. However, these models are expensive and time-consuming and most importantly they do not retain the original tumor microenvironment, which can have a marked effect on drug sensitivity [Straussman et al. (2012) *Nature* 487, 500-504].

Ex-vivo organ culture (EVOC) systems used in cancer biology are cultures of precision-cut slices of the patient's tumor. EVOC has been used for diverse applications including the study of drug toxicity, viral uptake, susceptibility of tumors to radiation or specific anti-cancer drugs [see e.g. Vaira et al. (2010) *Proc. Natl. Acad. Sci. U.S.A* 107, 8352-8356; Vickers et al. (2004) *Chem. Biol. Interact.* 150, 87-96; de Kanter et al. (2002) *Curr. Drug Metab.* 3, 39-59; Stoff-Khalili et al. (2005) *Breast Cancer Res. BCR* 7, R1141-1152; Merz et al. (2013) *Neuro-Oncol.* 15, 670-681; Gerlach et al. (2014) *Br. J. Cancer* 110, 479-488; Meijer et al. (2013) *Br. J. Cancer* 109, 2685-2695; Grosso et al. (2013) *Cell Tissue Res.* 352, 671-684; Vaira et al. (2010) *PNAS* 107, 8352-8356; Roife et al. (2016) *Clin. Cancer Res*. June 3, 1-10; Maund et al. (2014) *Lab. Invest.* 94, 208-221; Vickers et al. (2004) Toxicol Sci. 82(2):534-44; Zimmermann et al. (2009) *Cytotechnology* 61(3): 145-152); Parajuli et al. (2009) *In Vitro Cell.Dev.Biol.—Animal* 45:442-450; Koch et al. (2014) *Cell Communication and Signaling* 12:73; Graaf et al. *Nature Protocols* (2010) 5: 1540-1551; Majumder et al. *Nat. Commun.* 6, 6169 (2015); US Patent Application Publication Nos: US 2014/0228246, US 2010/0203575 and US 2014/0302491; and International Patent Application Publication No: WO2002/044344.

SUMMARY OF THE INVENTION

According to an aspect of some embodiments of the present invention there is provided a culture system comprising a culture medium and a precision-cut tissue slice placed on a tissue culture insert, wherein the precision-cut tissue slice is maintained in a highly oxygenated atmosphere containing at least 50% oxygen and wherein the culture is rotationally agitated facilitating intermittent submersion of the tissue slice in the culture medium.

According to some embodiments of the invention, the culture is in a tissue culture plate.

According to some embodiments of the invention, the culture system comprising a drug.

According to an aspect of some embodiments of the present invention there is provided a method of culturing a tissue, the method comprising culturing a precision-cut tissue slice on a tissue culture insert in culture medium under a highly oxygenated atmosphere containing at least 50% oxygen; and agitating the culture in a rotation facilitating intermittent submersion of the tissue slice in the culture medium.

According to some embodiments of the invention, the method further comprising adding a drug to the culture medium.

According to some embodiments of the invention, there is provided a method of determining efficacy of a drug or a batch of a drug, the method comprising:
  (i) culturing a tissue according to the method of the present invention;
  (i) adding the drug or the batch of a drug to the culture medium; and
  (iii) determining the effect of the drug or the batch of a drug on the tissue, wherein sensitivity of the tissue to the drug indicates efficacy of the drug.

According to some embodiments of the invention, the tissue is a pathological tissue.

According to some embodiments of the invention, there is provided a method of selecting a drug for the treatment of a disease in a subject in need thereof, the method comprising:
  (i) culturing a pathological tissue obtained from the subject according to the method of the present invention;
  (ii) adding the drug to the culture medium; and
  (iii) determining the effect of the drug on the tissue, wherein sensitivity of the tissue to the drug indicates efficacy of the drug for the treatment of the disease in the subject.

According to some embodiments of the invention, there is provided a method of treating a disease in a subject in need thereof, the method comprising:
  (a) selecting a drug according to the method of the present invention; and
  (b) administering to the subject a therapeutically effective amount of a drug demonstrating efficacy for the treatment of the disease in the subject, thereby treating the disease in the subject.

According to some embodiments of the invention, the drug is a drug combination.

According to some embodiments of the invention, the tissue or the precision-cut tissue slice is freshly isolated.

According to some embodiments of the invention, the tissue or the precision-cut tissue slice is preserved at 4° C.

According to some embodiments of the invention, the tissue or the precision-cut tissue slice is cryopreserved.

According to some embodiments of the invention, the determining is effected by morphology evaluation, viability evaluation, proliferation evaluation and/or cell death evaluation.

According to some embodiments of the invention, the determining is effected by morphology evaluation.

According to some embodiments of the invention, the determining is effected within 3-5 days of culturing.

According to some embodiments of the invention, the disease is cancer.

According to some embodiments of the invention, the cancer is selected from the group consisting of ovarian, colorectal, lung, pancreas, gastric, gastro esophageal and breast.

According to some embodiments of the invention, the pathological tissue is a cancerous tissue.

According to some embodiments of the invention, the tissue is selected from the group consisting of ovarian, colorectal, lung, pancreas gastric, gastro esophageal and breast.

According to some embodiments of the invention, the tissue is selected from the group consisting of ovarian, colorectal, lung, pancreas gastric, gastro esophageal, breast, liver, cartilage and bone.

According to some embodiments of the invention, the adding is effected 12-24 hours following the beginning of the culturing.

According to some embodiments of the invention, the drug is an anti-inflammatory drug or an anti-cancer drug.

According to some embodiments of the invention, the drug is selected from the group consisting of 5-fluorouracil (5FU), oxaliplatin, irinotecan, cisplatin, 4-hydroperoxy cyclophosphamide, docetaxel, doxorubicin, navalbine, gemcitabine, gefitinib, tamoxifen, olaparib, trametinib, everolimus and palbociclib.

According to some embodiments of the invention, the drug concentration is higher than the drug IC50 dose in a cell line.

According to some embodiments of the invention, the drug concentration is derived from a dosing experiment wherein a dose-dependent response is observed.

According to some embodiments of the invention, the culturing is effected for at least 4 days.

According to some embodiments of the invention, the culturing is effected for at least 5 days.

According to some embodiments of the invention, the culturing is effected for up to 7 days.

According to some embodiments of the invention, the culturing is effected in a tissue culture plate.

According to some embodiments of the invention, the precision-cut slice is 200-300 µm.

According to some embodiments of the invention, the slice is placed in the middle of the cell culture insert.

According to some embodiments of the invention, the slice is one slice.

According to some embodiments of the invention, the slice is in direct contact with the tissue culture insert.

According to some embodiments of the invention, the tissue culture insert is a titanium grid insert.

According to some embodiments of the invention, the tissue is a human tissue.

According to some embodiments of the invention, the highly oxygenated atmosphere contains at least 70% oxygen.

According to some embodiments of the invention, the highly oxygenated atmosphere contains less than 95% oxygen.

According to some embodiments of the invention, the method is effected in combination with genetic profiling.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
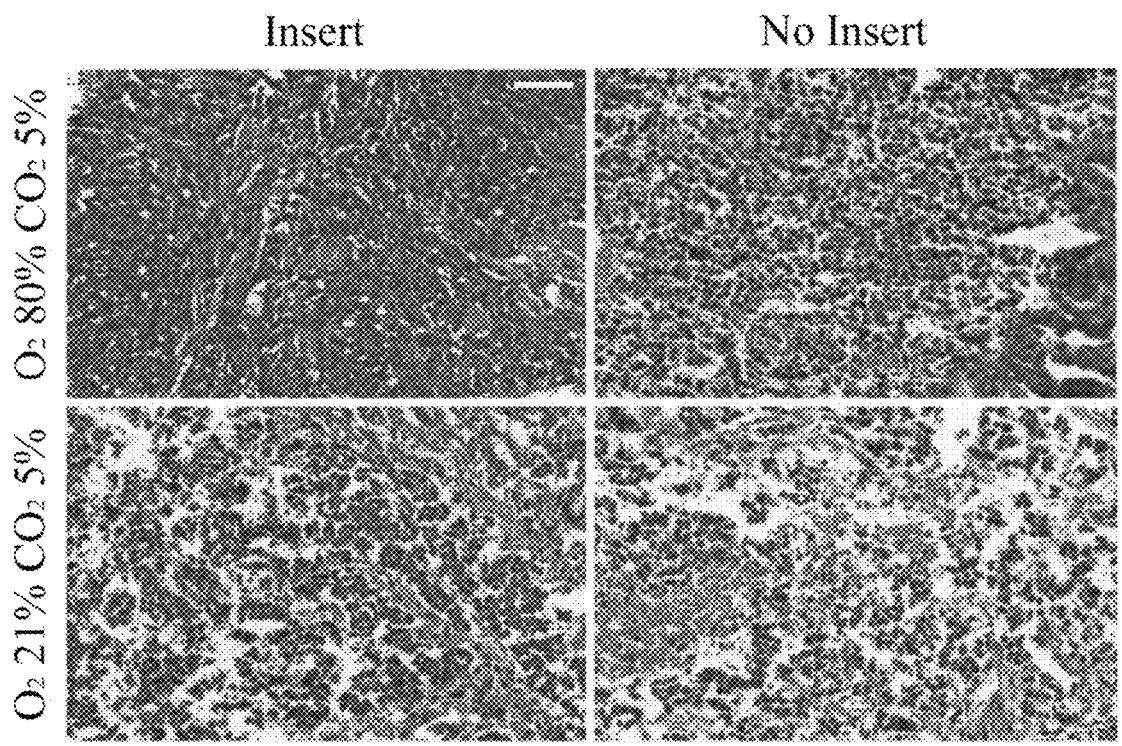

FIG. 1 shows representative histological photomicrographs demonstrating the morphology of slices of human ovarian cancer derived xenografts following 5 days of ex-vivo culturing. Precision-cut slices of the harvested tissue were incubated on titanium insert (left column) in a 6-well plate, or directly in the 6-well plate (right column); in 21% $O_2$ (bottom row) or in 80% $O_2$ (upper row) for 5 days; and stained with H&E. Scale bar represents 50 µm. For each condition tissues were tested in triplicate.

Figure 2:
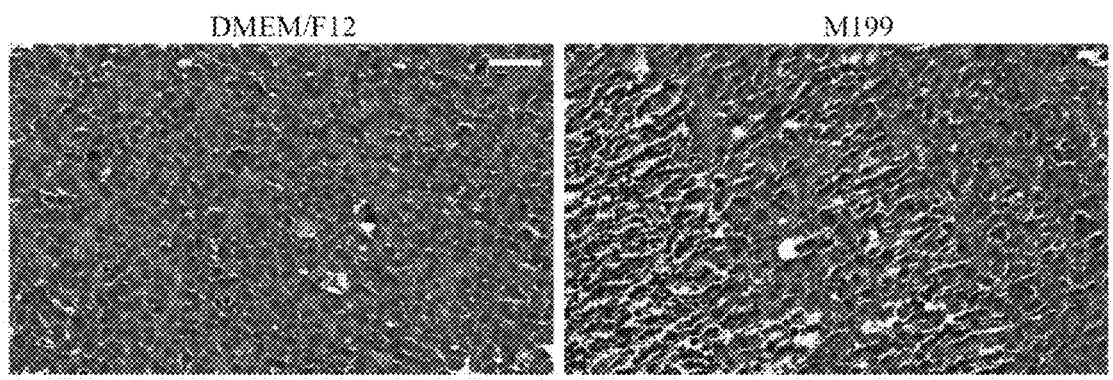

FIG. 2 shows representative histological photomicrographs demonstrating the morphology of slices of human breast cancer derived xenografts following 5 days of ex-vivo culturing in different media. Precision-cut slices of the harvested tissue was incubated on titanium insert in 80% $O_2$ in DMEM/F12 (left panel) or M199 (right panel) media for 5 days; and stained with H&E. Scale bar represents 50 µm. For each condition tissues were tested in duplicate.

Figure 3:
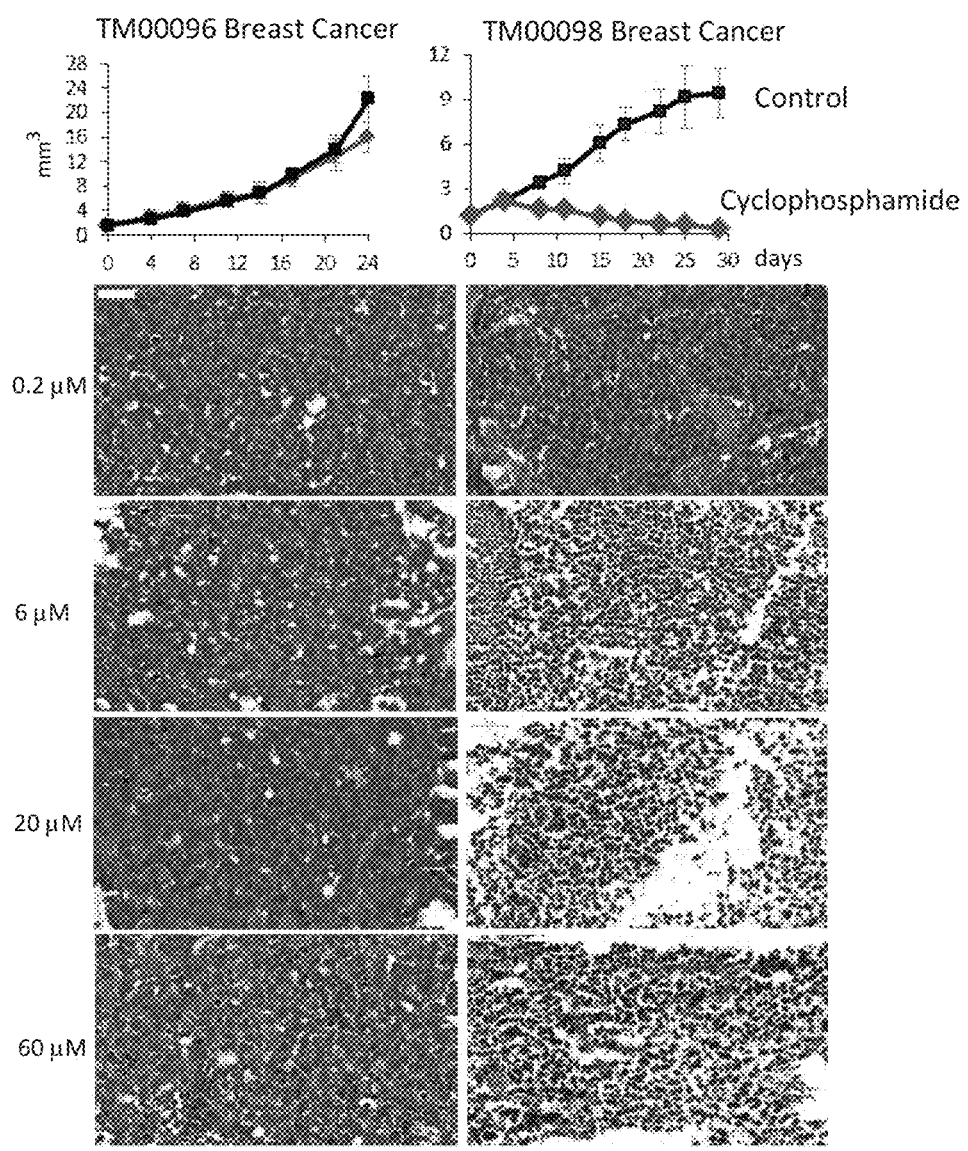

FIG. 3 demonstrates the ability of the developed ex-vivo culturing method to predict responses of human breast carcinoma derived xenografts to an anti-cancer drug treatment. Shown are graphs generated by Jackson Laboratories demonstrating the in-vivo response of two human breast carcinoma derived xenografts to treatment with 4-hydroperoxy cyclophosphamide, indicating that the TM00096 breast carcinoma is resistant to treatment while the TM00098 breast carcinoma is sensitive to treatment. The y-axis indicates tumor size in $mm^3$.

Figure 4:
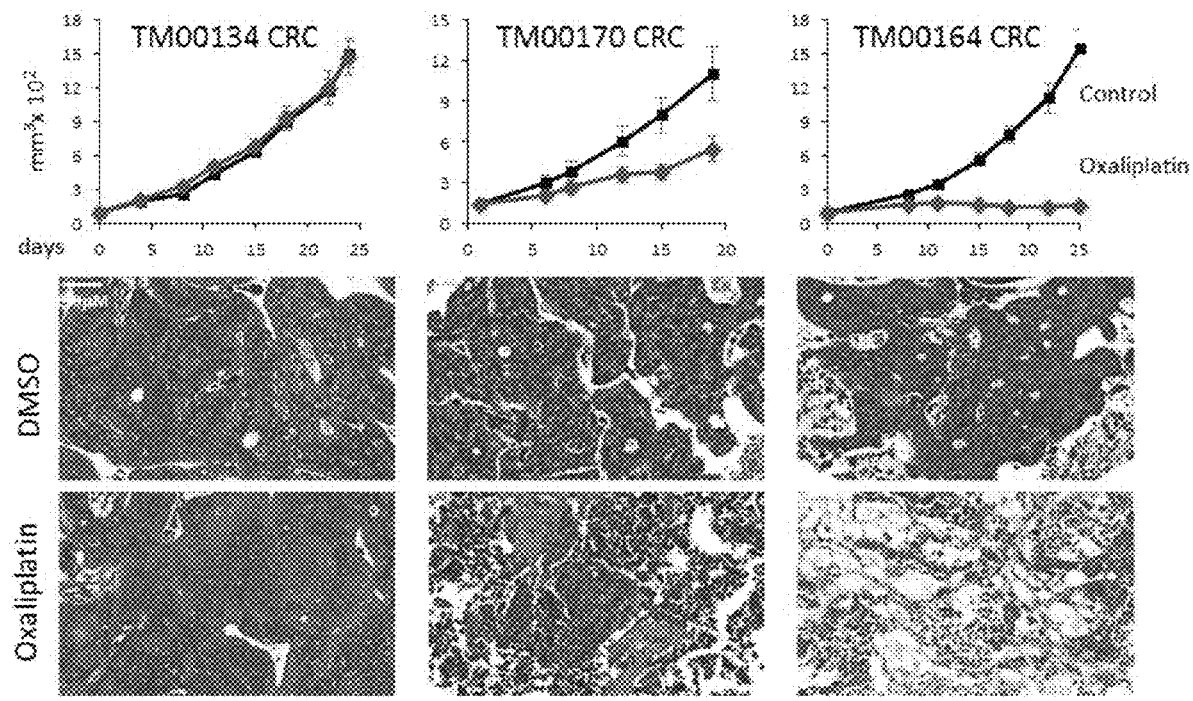

The representative histological photomicrographs demonstrate the morphology of slices of the TM00096 (left column) and TM00098 (right column) breast carcinomas following 5 days of ex-vivo culturing on titanium insert in 80% O$_2$ treated for 4 days with the indicated concentrations of 4-hydroperoxy cyclophosphamide. Scale bar represents 50 μm. For each condition tissues were tested in duplicate;

FIG. 4 demonstrates the ability of the developed ex-vivo culturing method to predict response of human colorectal carcinoma (CRC) derived xenografts to an anti-cancer drug treatment. Shown are graphs generated by Jackson Laboratories demonstrating the in-vivo response of three CRC derived xenografts to treatment with oxaliplatin, indicating the TM00134 CRC is resistant to treatment while the TM00170 tumor is partially sensitive and the TM00164 CRC is very sensitive to treatment. The y-axis indicates tumor size in mm$^3$.

The representative histological photomicrographs demonstrate the morphology of slices of the TM00134 (left panel), TM00170 (middle panel) and TM00164 (right panel) CRC following 5 days of ex-vivo culturing on titanium insert in 80% O$_2$ treated for 4 days with 0.2 μM oxaliplatin. Treatment with DMSO served as control. Scale bar represents 50 μm. For each condition tissues were tested in triplicate.

Figure 5:
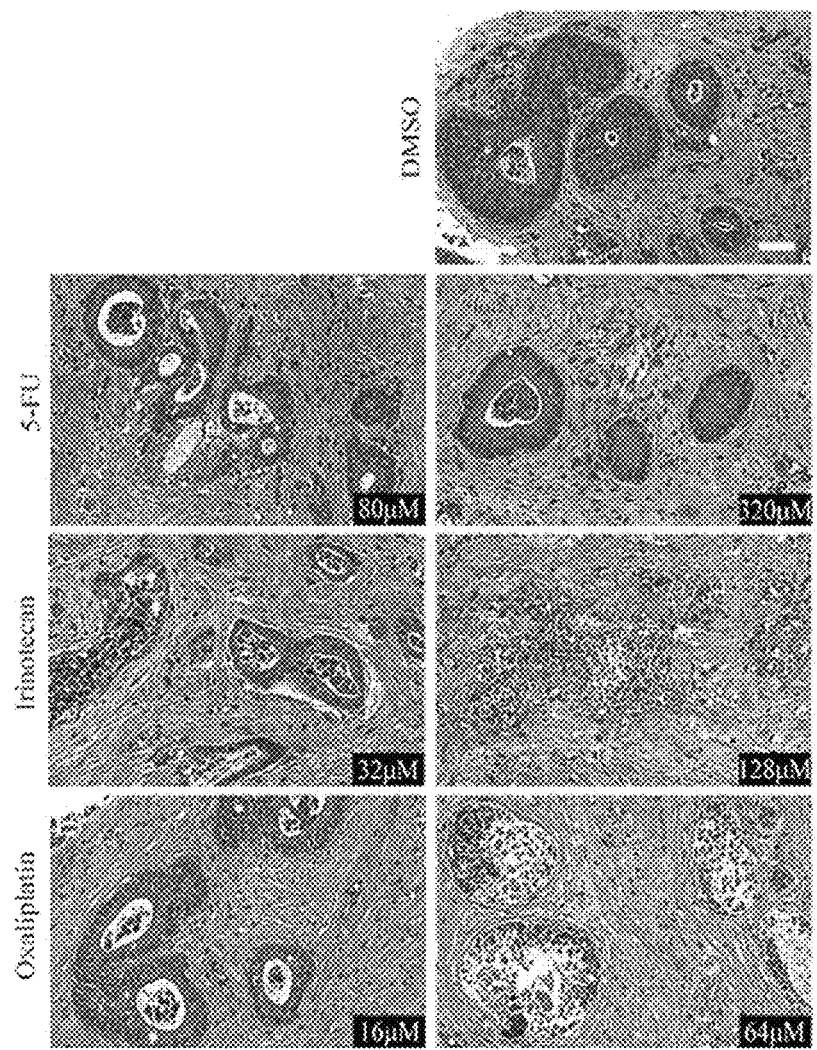
Figure 6:
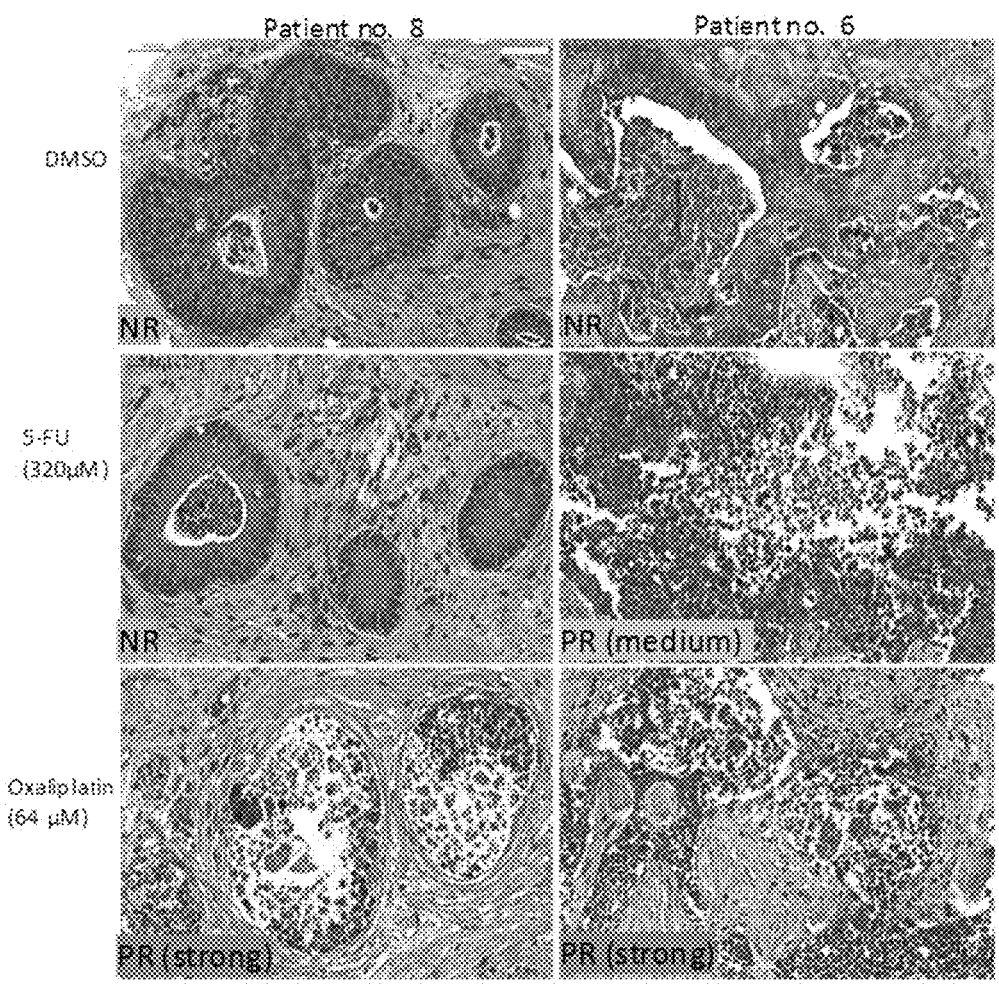

FIG. 5 demonstrates that tumor tissue slices cultured under the developed ex-vivo culturing method present differential sensitivity to different anti-cancer drugs. The human colorectal cancer (CRC) tumor tissue was taken from a metastatic lesion in the peritoneum removed during an operation for de-bulking and intraperitoneal chemotherapy. Shown are representative histological photomicrographs demonstrating the morphology of tumor slices following 5 days of ex-vivo culturing on titanium insert in 80% O$_2$ treated for 4 days with the indicated anti-cancer drugs 5-fluorouracil (5 FU), irinotecan or oxaliplatin. Treatment with DMSO served as control. Note that the tissue was sensitive to oxaliplatin and irinotecan treatment in a dose dependent manner but resistant to 5-fluorouracil. Scale bar represents 50 μm. For each condition tissues were tested in triplicate;

FIG. 6 demonstrates that tumor tissue slices obtained from different individuals and cultured under the developed ex-vivo culturing method present differential sensitivity to the same anti-cancer drug. The human colorectal cancer (CRC) tumor tissue was taken from a metastatic lesion in the peritoneum removed during an operation for de-bulking and intraperitoneal chemotherapy. Shown are representative histological photomicrographs demonstrating the morphology of slices of the tumor following 5 days of ex-vivo culturing on titanium insert in 80% O$_2$ treated for 4 days with the indicated anti-cancer drugs: 5-fluorouracil (5 FU) or oxaliplatin. Treatment with DMSO served as control. PR indicates partial response; and NR indicates no response. Note that while the tumor obtained from patient no. 8 had a strong partial response to oxaliplatin and no response to 5-fluorouracil the other patient, patient no. 6, partially responded to both drugs. Scale bar represents 50 μm. For each condition tissues were tested in duplicate.

Figure 7:
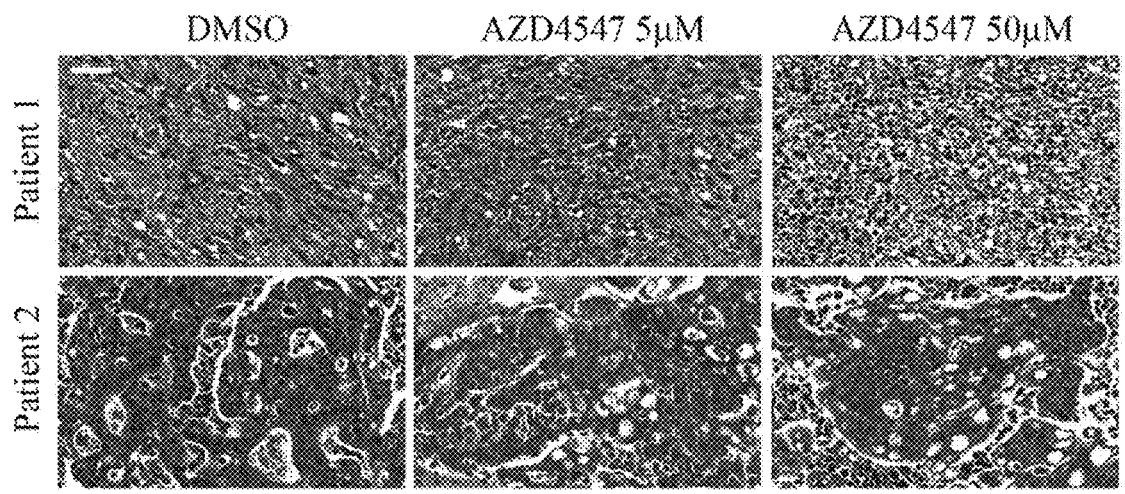

FIG. 7 demonstrates the ability of the developed ex-vivo culturing method to predict sensitivity to targeted therapy as predicted by molecular profiling. Shown are representative histological photomicrographs demonstrating the morphology of slices of triple negative breast cancer tumors from two patients following 5 days of ex-vivo culturing on titanium insert in 80% O$_2$ treated for 4 days with AZD4547 (an FGFR inhibitor). Treatment with DMSO served as control. Note that Patient no. 1 whose tumor harbors an amplification of FGFR1 was sensitive to AZD4547 (an FGFR inhibitor) while patient no. 2 who does not harbor this mutation was resistant to treatment. Scale bar represents 50 μm. For each condition tissues were tested in duplicate.

Figure 8:
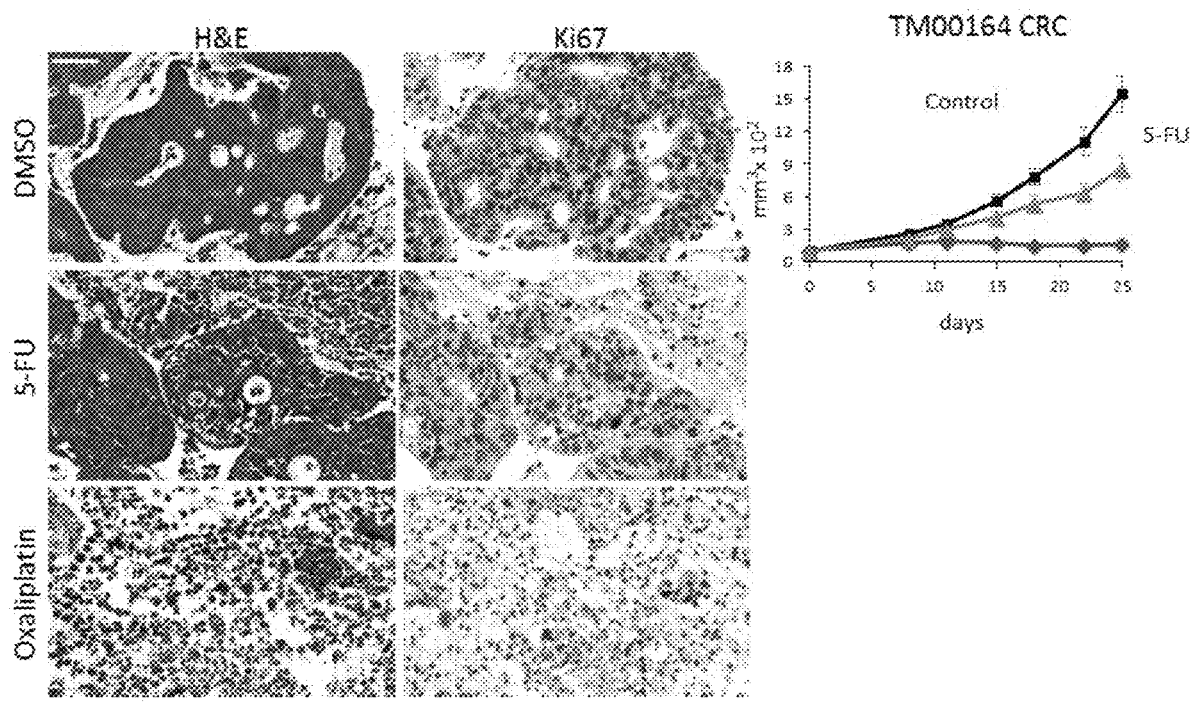
Figure 9:
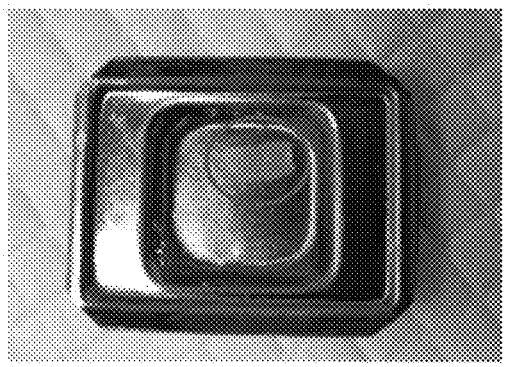
Figure 9:
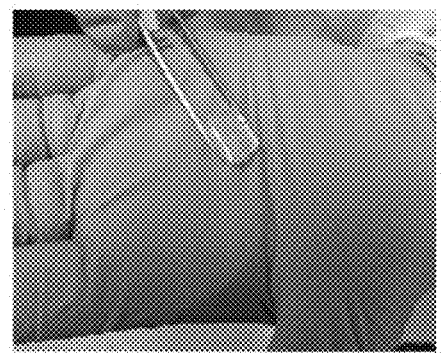
Figure 9:
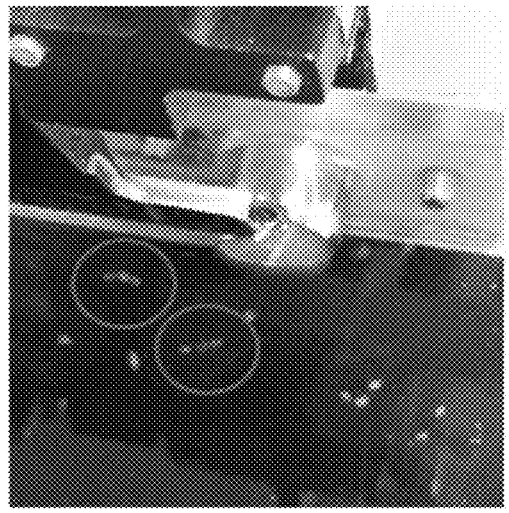
Figure 9:
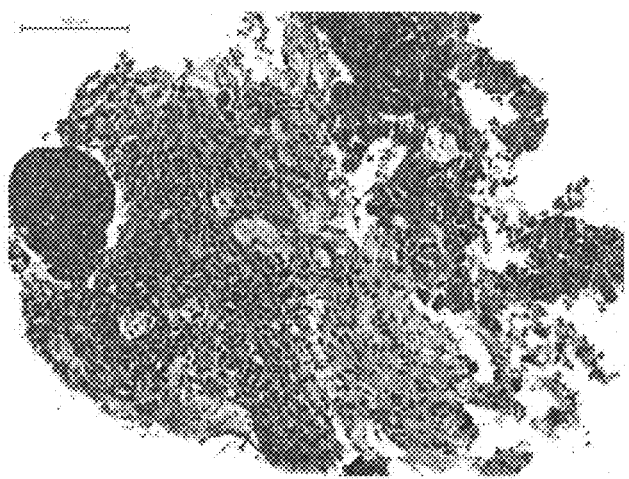

FIG. 8 demonstrates that staining with Ki67 for proliferation can be used to evaluate the sensitivity of tissue to different treatments. Shown are representative histological photomicrographs demonstrating the morphology (by H&E staining) and proliferation (by Ki67 staining) from one patient following 5 days of ex-vivo culturing on titanium insert in 80% O$_2$ treated for 4 days with the indicated drugs. The graph on the right, generated by Jackson Laboratories, demonstrates the in-vivo response of this CRC derived xenograft to treatment with oxaliplatin and 5-fluorouracil. The y-axis indicates tumor size in mm$^3$. This patient was partially sensitive to 5-Fluouricil but very sensitive to oxaliplatin both in-vivo and ex-vivo. DMSO treatment served as control. Scale bar represents 50 μm. For each condition tissues were tested in duplicate. FIG. 9 demonstrates processing of core biopsies for EVOC. In this example three core biopsies are placed one beside the other in liquid agarose in a metal tray. More agarose is added and the tray is cooled. The biopsies are cut out of the agarose and the block is fixed on the plunger with contact glue, embedded in more agarose (using the same method as with tissue pieces) and then cut with the microtome. The biopsy slices are treated and processed in a manner similar to tissue slices. Scale bar represents 100 μm.

Figure 10:
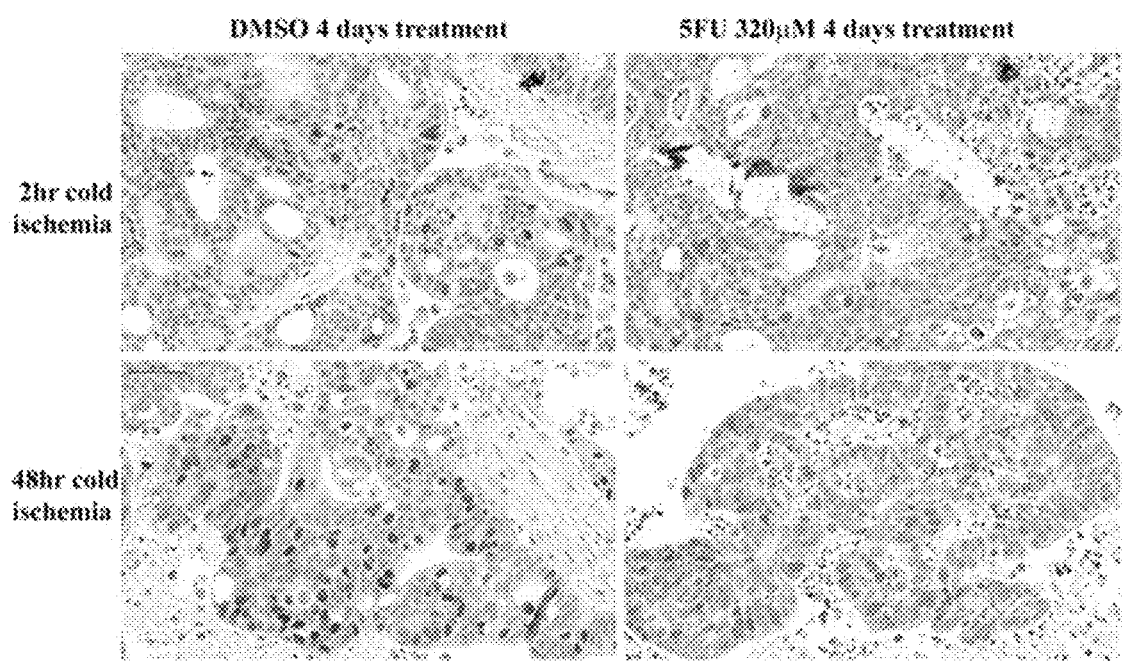

FIG. 10 shows histological photomicrographs demonstrating that tissue can be sliced and stored in medium for up to 48 hours prior to beginning experimentation without any adverse effects to the tissue or any change in the outcome. Shown is a colon cancer tissue that was treated with control DMSO or 5-fluorouracil (5-FU) for 4 days either immediately following slicing or 48 hours following refrigeration. BrdU was added 18 hours prior to the end of the experiment; and the tissue was stained with anti-BrdU antibody to identify dividing cells. Note that tissue treated with 5-FU is still somewhat viable but is started to respond to treatment with increased cell death and less BrdU in both conditions. Scale bar represents 50 μM.

Figure 11:

FIG. 11 shows representative histological images demonstrating the indicated tissues following 5 days of ex-vivo culturing; and a Table summarizing the tissues examined which all maintained the structure and viability of the tissue for at least 5 days of culture. Precision-cut slices of the harvested tissue were incubated on titanium insert in DMEM/F12 in 80% O$_2$ for 5 days; and stained with H&E. All experiments were performed in duplicates on two different cases of the indicated cancer

DESCRIPTION OF SPECIFIC EMBODIMENTS OF THE INVENTION

The present invention, in some embodiments thereof, relates to an ex-vivo culture system and methods of using same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Personalized treatment options for diseases such as cancer typically employs genetic profiling and testing the response of patient's cells to a specific treatment using expensive and time-consuming models such as the tumor derived cell lines generated from patients' tumors and patient-derived xenograft (PDX) models. In recent years ex-vivo organ culture (EVOC) systems were suggested for use in diverse applications including the study of drug toxicity, viral uptake, susceptibility of tumors to radiation or specific anti-cancer drugs.

Whilst reducing the present invention to practice, the present inventors have now developed an EVOC system which can preserve the structure and viability of a precision-cut tissue slice for up to 7 days in culture and as such can predict response of pathological tissues to various drugs.

As is illustrated hereinunder and in the examples section, which follows, the newly developed EVOC system is based on culturing one slice of tissue directly placed on a culture insert (in this case, in the middle of a titanium reusable grid) that allows intermittent submersion of the slice in the medium, thereby facilitating nutrient and gas diffusion throughout the slice, in highly oxygenated atmosphere containing oxygen (80%) using standard medium with only the addition of fetal-calf serum (FCS) and antimicrobials (Example 1, Table 1, FIGS. 1-2 and 9). EVOC systems of various cancerous tissues including ovarian, colorectal, lung, pancreas and breast tissue cultured according to this method presented high viability following 4-6 days in culture (Example 1, Table 1, FIG. 11).

Following, the present inventors show that the developed EVOC system can be used for predicting response of tumors to anti-cancer drugs (Example 2). Specifically, the present inventors demonstrate that the sensitivity of ex-vivo cancerous tissue slices obtained from various patient-derived xenografts (PDX) models to anti-cancer treatment is consistent with the in-vivo response of the PDX models to treatment (Example 2, Table 2, FIGS. 3-4); and that sensitivity of ex-vivo triple negative breast cancer tissue slices obtained from patients to targeted therapy is consistent with the molecular profiling data (Example 2, FIG. 7). Moreover, the present inventors show that EVOC systems of human tumors from various patients present differential sensitivity to different anti-cancer treatments (Example 2, Tables 3-4, FIGS. 5-6 and 8). Importantly, the tissue can be stored in medium for at least 48 hours prior to beginning of experimentation without any adverse effects on the tissue or drug sensitivity (Example 2, FIG. 10).

Taken together, the newly developed EVOC system preserves tissue microenvironment, architecture, viability and genetic heterogeneity. This system enables studying a human tissue (e.g. cancer tissue) response in a fast, reliable and cost effective manner. Consequently, the present teachings further suggest the use of this developed EVOC system for pre-clinical and basic research as well as for qualifying efficacy of a drug for disease treatment in general and for personalized therapy in particular.

Thus, according to a first aspect of the present invention, there is provided a culture system comprising a culture medium and a precision-cut tissue slice placed on a tissue culture insert, wherein said precision-cut tissue slice is maintained in a highly oxygenated atmosphere containing at least 50% oxygen and wherein said culture is rotationally agitated facilitating intermittent submersion of said tissue slice in said culture medium.

According to another aspect of the present invention, there is provided a method of culturing a tissue, the method comprising culturing a precision-cut tissue slice on a tissue culture insert in culture medium under a highly oxygenated atmosphere containing at least 50% oxygen; and agitating the culture in a rotation facilitating intermittent submersion of said tissue slice in said culture medium As used herein, the term "culture system" refers to at least a precision-cut tissue slice, insert and medium in an ex-vivo environment.

According to specific embodiments, the culture system maintains structure and viability of the precision-cut tissue slice for at least 2-10, 2-7, 2-5, 4-7, 5-7 or 4-5 days in culture. According to a specific embodiment, the precision-cut tissue slice maintains viability for at least 5 days, 6 days, 7 days or even 10 days. According to a specific embodiment, the precision-cut tissue slice maintains viability for at least 5 days.

According to specific embodiments, at least 60%, at least 70%, at least 80% of the cells in the precision-cut tissue maintain viability following 4-5 days in culture as determined by e.g. morphology analysis of an optimal area of viability.

As used herein, the phrase "optimal area of viability" refers to a microscopic field of the tissue (e.g. in 20× magnification) in which the highest number of live cells per unit area are present, as assessed by a pathologist, in comparison to the immediate pre-EVOC sample of the same species.

Thus, according to specific embodiments, the culturing is effected for 2-10, 2-7, 2-5, 4-7, 5-7 or 4-5 days.

According to a specific embodiment, the culturing is effected for at least 4 days.

According to a specific embodiment, the culturing is effected for at least 5 days.

According to a specific embodiment, the culturing is effected for up to 7 days.

As used herein the term "tissue" refers to part of a solid organ (i.e., not blood) of an organism having some vascularization that includes more than one cell type and maintains at least some macro structure of the in-vivo tissue from which it was excised.

Examples include, but are not limited to, ovarian tissue, colorectal tissue, lung tissue, pancreatic tissue, breast tissue, brain tissue, retina, skin tissue, bone, cardiac tissue and renal tissue. According to specific embodiments, the tissue is selected from the group consisting of ovarian, colorectal, lung, pancreas, gastric, gastro esophageal and breast. According to specific embodiments, the tissue is selected from the group consisting of ovarian, colorectal, lung, pancreas gastric, gastro esophageal, breast, liver, cartilage and bone. According to specific embodiments the tissue is a metastatic cancer tissue obtained from sites such as, but not limited to the liver, the bone, the lung and the peritoneum.

According to specific embodiments, the tissue is not a liver tissue.

According to specific embodiments, the tissue is not a prostate tissue.

According to specific embodiments, the tissue is a mammalian tissue.

According to a specific embodiment, the tissue is a human tissue.

According to another specific embodiment, the tissue is a mouse or rat tissue.

According to specific embodiments, the tissue is a healthy tissue.

According to other specific embodiments, the tissue is a pathological tissue. The method may employ a plurality of screened precision-cut tissue slices (e.g., each on a separate insert), all of which can be from a pathological tissue(s), healthy tissue(s) or a combination of same (e.g., when the healthy tissue serves as control when taken from the same tissue origin as the pathological tissue).

According to specific embodiments the tissue is a pathological tissue.

As used herein the term "pathological tissue" refers to a tissue causing a disease. Hence, elimination of such a tissue is expected to lead to treatment as further defined hereinbelow. Specific examples of diseases amenable to treatment according to some embodiments of the present invention are described in details hereinbelow. According to specific embodiments the pathological tissue is an inflamed tissue, a fibrotic tissue or a cancerous tissue. According to a specific embodiment, the pathological tissue is a cancerous tissue.

According to specific embodiments the tissue is obtained surgically or by biopsy, laparoscopy, endoscopy or as xenograft or any combinations thereof.

The tissue may be cut and cultured directly following tissue extraction (i.e. primary tissue) or following implantation in an animal model [i.e. a patient-derived xenograft (PDX)], each possibility represents a separate embodiment of the present invention.

The tissue or the tissue slice to some embodiments of the present invention can be freshly isolated or stored e.g., at 4° C. or cryopreserved (i.e. frozen) at e.g. liquid nitrogen.

According to specific embodiments, the tissue or the tissue slice is freshly isolated (i.e., not more than 24 hours after retrieval from the subject and not subjected to preservation processes), as further disclosed hereinbelow.

According to specific embodiments, the tissue is cryopreserved following tissue retrieval and prior to cutting.

According to specific embodiments, the tissue is thawed prior to cutting.

According to specific embodiments, the tissue slice is cryopreserved following cutting.

According to specific embodiments, the tissue slice is thawed prior to culturing.

According to specific embodiments, the tissue is preserved at 4° C. in e.g. medium following tissue retrieval and prior to cutting.

According to specific embodiments the tissue slice is preserved at 4° C. in e.g. medium following cutting and prior to culturing.

According to specific embodiments, the preservation at 4° C. is effected for up to 120 hours, up to 96 hours, up to 72 hours or up to 48 hours.

According to specific embodiments, the preservation at 4° C. is effected for 24-48 hours.

Thus, according to specific embodiments, the method further comprises obtaining the tissue from the subject or from the animal model comprising the tissue.

As used herein the phrase "patient-derived xenograft (PDX)" refers to tissue generated by the implantation of a primary tissue into an animal from a different species relative to the donor of the primary tissue. According to specific embodiments the PDX is a tissue generated by implantation of a human primary tissue (e.g. cancerous tissue) into an immunodeficient mouse.

Following tissue extraction the tissue is sliced to precision-cut slices.

As used herein, the phrase "precision-cut tissue slice" refers to a viable slice obtained from an isolated solid tissue with reproducible, well defined thickness (e.g. ±5% variation in thickness between slices).

Typically, the tissue slice is a mini-model of the tissue which contains the cells of the tissue in their natural environment and retains the three-dimensional connectivity such as intercellular and cell-matrix interactions of the intact tissue with no selection of a particular cell type among the different cell type that constitutes the tissue or the organ. Precision-cutting reduces sources of error due to variations in slice thickness and damage to cut surfaces, which both contribute to uneven gas and nutrient exchange throughout tissue slices; it enhances reproducibility; and allows adjacent slices to be evaluated for histology and compared pair-wise under different experimental conditions.

The slice section can be cut in different orientations (e.g. anterior-posterior, dorsal-ventral, or nasal-temporal) and thickness. The size/thickness of the tissue section is based on the tissue source and the method used for sectioning. According to specific embodiment the thickness of the precision-cut slice allows maintaining tissue structure in culture.

According to specific embodiments the thickness of the precision-cut slice allows full access of the inner cell layers to oxygen and nutrients, such that the inner cell layers are exposed to sufficient oxygen and nutrients concentrations.

According to specific embodiments the thickness of the precision-cut slice allows full access of the inner cell layers to oxygen and nutrients, such that the inner cell layers are exposed to the same oxygen and nutrients concentrations as the outer cell layers.

According to specific embodiments, the precision-cut slice is between 50-1200 μm, between 100-1000 μm, between 100-500 μm, between 100-300 μm, or between 200-300 μm.

According to a specific embodiment, the precision-cut slice is 200-300 μm.

Methods of obtaining tissue slices are known in the art and described for examples in the Examples section which follows and in Roife et al. (2016) *Clin. Cancer Res*. June 3, 1-10; Vickers et al. (2004) Toxicol Sci. 82(2):534-44; Zimmermann et al. (2009) *Cytotechnology* 61(3): 145-152); Koch et al. (2014) *Cell Communication and Signaling* 12:73; and Graaf et al. *Nature Protocols* (2010) 5: 1540-1551, the contents of each of which are fully incorporated herein by reference. Such methods include, but are not limited to slicing using a vibratome, agarose embedding followed by sectioning by a microtome, or slicing using a matrix.

As a non-limiting example, the tissue is isolated and immediately placed in a physiological dissection media (e.g. ice cold PBS) which may be supplemented with antibiotics.

According to specific embodiments, the warm ischemic time is less than 2 hours, less than 1.5 hours or less than 1 hour.

According to specific embodiments, the cold ischemic time is less than 96 hours, less than 72 hours, less than 48 hours, less than 24 hours, less than 12 hour, less than 5 hours or less than 2 hours.

Prior to slicing, the tissue is attached to the tissue slicer using e.g. contact glue followed by embedding in e.g. low melting agarose gel. Subsequently, the tissue is sectioned into precision-cut slices. Numerous suitable tissue sectioning devices are commercially available, such as, but not limited to Compresstome™ VF-300 (Precisionary Instruments Inc. NC, USA), Brendel-Vitron tissue slicer (Tucson, AZ), Krumdieck precision tissue slicer (model no. MD4000-01; Alabama R&D) and Leica VT1200S vibrating blade microtome (Leica, Wetzlar, Germany). According to specific embodiments, the sectioning devise is filled with ice cold medium such as Williams Medium E or Krebs-Henseleit buffer (KHB). The skilled artisan would know which medium and conditions for dissection and for preserving the tissue and the tissue slice prior to culturing for each type of tissue.

Following, the tissue slice is placed on a tissue culture insert in a tissue culture vessel filled with culture medium. One slice or multiple slices can be placed on a single tissue culture insert. According to specific embodiments, one slice is placed on a single tissue culture insert.

According to specific embodiments, the culture vessel is filled with culture medium up to the bottom of the tissue slice (e.g. 4 ml of medium in a 6-well plate containing an insert).

The culture may be in a glass, plastic or metal vessel that can provide an aseptic environment for tissue culturing. According to specific embodiments, the culture vessel includes dishes, plates, flasks, bottles and vials. Culture vessels such as COSTAR®, NUNC® and FALCON® are commercially available from various manufacturers.

According to specific embodiments, the culture vessel is a tissue culture plate such as a 6-wells plate, 24-wells plate, 48-wells plate and 96-wells plate.

According to a specific embodiment, the culture vessel is a tissue culture 6-wells plate.

According to specific embodiments, the culture vessel is not pre-coated with proteins extracted from a matched tissue (e.g. when the tissue is a cancerous tissue, then the culture vessel is not pre-coated with stage and grade-matched tumor extracted proteins). Non limiting examples for such proteins include ECM proteins such as collagen, fibronectin, laminin, vibronectin, cadherin, filamin A, vimentin, osteopontin, Decorin, tenascin X, basement membrane proteins, cytoskeletal proteins and matrix proteins; and growth factors.

The culture medium used by the present invention can be a water-based medium which includes a combination of substances such as salts, nutrients, minerals, vitamins, amino acids, nucleic acids and/or proteins such as cytokines, growth factors and hormones, all of which are needed for cell proliferation and are capable of maintaining structure and viability of the tissue. For example, a culture medium can be a synthetic tissue culture medium such as DMEM/F12 (can be obtained from e.g. Biological Industries), M199 (can be obtained from e.g. Biological Industries), RPMI (can be obtained from e.g. Gibco-Invitrogen Corporation products), M199 (can be obtained from e.g. Sigma-Aldrich), Ko-DMEM (can be obtained from e.g. Gibco-Invitrogen Corporation products), supplemented with the necessary additives as is further described hereinunder. Preferably, all ingredients included in the culture medium of the present invention are substantially pure, with a tissue culture grade.

The skilled artisan would know to select the culture medium for each type of tissue contemplated.

According to specific embodiments of the invention, the culture medium comprises serum e.g. fetal calf serum (FCS, can be obtained e.g. from Gibco-Invitrogen Corporation products).

According to specific embodiments, the culture medium comprises less than 10% serum.

According to specific embodiments, the culture medium comprises less than 2% serum obtained from the same species as the cultured tissue.

According to specific embodiments, the culture medium is devoid of serum obtained from the same species as the cultured tissue.

According to specific embodiments, the culture medium comprises less than 2% serum autologous to the cultured tissue (i.e. from the same subject).

According to specific embodiments, the culture medium is devoid of serum autologous to the cultured tissue (i.e. from the same subject).

According to specific embodiments, the culture medium comprises less than 2% human serum.

According to some embodiments of the invention, the culture medium is devoid of human serum.

According to some embodiments of the invention, the culture medium is devoid of any animal contaminants, i.e., animal cells, fluid or pathogens (e.g., viruses infecting animal cells), i.e., being xeno-free.

According to some embodiments of the invention, the culture medium can further include antibiotics (e.g., penicillin, streptomycin, gentamycin), anti-fungal agents (e.g. amphotericin B), L-glutamine or NEAA (non-essential amino acids).

According to a specific embodiment, the medium comprises serum and antibiotics.

According to a specific embodiment, the medium comprises DMEM/F12, 5% FCS, glutamine, penicillin, streptomycin, gentamycin and amphotericin B It should be noted that the culture medium may be periodically refreshed to maintain sufficient levels of supplements and to remove metabolic waste products that can damage the tissue. According to specific embodiments, the culture medium is refreshed every 12-72 hours, every 24-72 hours, every 24-48 hours or every 12-48 hours.

According to specific embodiments, the culture medium is refreshed every 12-48 hours.

According to a specific embodiment, the culture medium is refreshed once after 12-24 hours and then every about 48 hours.

As used herein, the phrase "tissue culture insert" refers to a porous membrane suspended in a vessel for tissue culture and is compatible with subsequent ex-vivo culturing of a tissue slice.

The pore size is capable of supporting the tissue slice while it is permeable to the culture medium enabling the passage of nutrients and metabolic waste to and from the slice, respectively. According to specific embodiments, the tissue slice is placed on the tissue culture insert, thereby allowing access of the culture medium to both the apical and basal surfaces of the tissue slice.

According to specific embodiments the pore size is 0.1 µm-20 µm, 0.1 µm-15 µm, 0.1 µm-10 µm, 0.1 µm-5 µm, 0.4 µm-20 µm, 0.4 µm-10 µm or 0.4 µm-5 µm.

According to specific embodiments the pore size is 0.4 mm-4 mm, 0.4 mm-1 mm, 1 mm-4 mm, 1 mm-3 mm or 1 mm-2 mm.

According to specific embodiments, the tissue culture insert is sterile.

According to specific embodiments, the tissue culture inset is disposable.

According to specific embodiments, the cell culture insert is re-usable and autoclavable.

The cell culture insert may be synthetic or natural, it can be inorganic or polymeric e.g. titanium, alumina, Polytetrafluoroethylene (PTFE), Teflon, stainless steel, polycarbonate, nitrocellulose and cellulose esters. According to specific embodiments, the cell culture insert is a titanium insert. Cell culture inserts that can be used with specific embodiments of the invention are commercially available from e.g. Alabama R&D, Millipore Corporation, Costar, Corning Incorporated, Nunc, Vitron Inc. and SEFAR and include, but not limited to MA0036 Well plate Inserts, BIOCOAT™, Transwell®, Millicell®, Falcon®-Cyclopore, Nunc® Anapore, titanium-screen and Teflon-screen.

According to specific embodiments, the tissue culture insert is a titanium grid insert, such as but not limited to Titanium MA0036 Well plate Inserts (Alabama R&D).

According to specific embodiments, the tissue culture insert is not coated with an organic material such as collagen, fibronectin or polyethylene glycol (PEG).

According to specific embodiments, the tissue culture insert is not coated with proteins extracted from a matched tissue (e.g. when the tissue is a cancerous tissue, then the tissue culture insert is not pre-coated with stage and grade-matched tumor extracted proteins).

According to specific embodiments, the tissue slice is in direct contact with the tissue culture insert.

According to specific embodiments, the tissue slice is not separated from the culture medium by a heterologous organic material such as collagen, fibronectin or synthetic polymer (which is not part of the culture vessel) e.g., polyethylene glycol (PEG).

According to specific embodiments, the tissue slice is in direct contact with the culture medium.

According to specific embodiments, the tissue slice is placed in the middle of the cell culture insert. Thus, for example, when a titanium grid such as the Titanium MA0036 Well plate Inserts is applied the tissue slice is placed in the concavity located at the middle of the insert.

Following, the tissue slice is cultured (or maintained) at a physiological temperature, e.g. 37° C., in a highly oxygenated humidified atmosphere containing at least 50% oxygen and e.g. 5% $CO_2$.

According to specific embodiments the highly oxygenated atmosphere contains at least 60%, at least 70% or at least 80% oxygen.

According to specific embodiments, the highly oxygenated atmosphere contains at least 70% oxygen.

According to other specific embodiments, the highly oxygenated atmosphere contains less than 95% oxygen.

According to a specific embodiment, the highly oxygenated atmosphere contains about 80% oxygen.

According to a specific embodiment, during the culturing process, the culture is agitated in a rotation facilitating intermittent submersion of the tissue slice in the culture medium.

As used herein the phrases "rotationally agitated facilitating intermittent submersion of the tissue slice in the culture medium" or "agitating in a rotation facilitating intermittent submersion of the tissue slice in the culture medium" refers to agitation which allows periodic submersion of the tissue slice in the medium such that facilitates nutrients and gas diffusion throughout the medium and through the tissue slice.

According to specific embodiments, the agitation is orbital agitation.

According to specific embodiments the agitation is an angled agitation, e.g. an angle of 30°-45°.

According to specific embodiments, the agitation is effected by an inclined rotator (such as the MD2500 incubation unit commercially available from Alabama Research and Development)

According to specific embodiments the agitation frequency is 50-200 rpm, 50-150 rpm or 50-100 rpm.

According to specific embodiment the agitation frequency is about 70 rpm.

The tissue culture and the methods of the present invention can be adapted to many applications, including, but not limited to:

1. Pre-clinical and basic research including:
    Studying mechanisms involved in health and disease;
    Screening a pathologic tissue (e.g. a tumor tissue) for the presence of specific markers;
    Screening and/or developing novel drugs such as anti-cancer drugs or novel drug combinations;
    Determining potency of a batch of a drug;
    Studying mechanisms of sensitivity and resistance of human tissues. Thus, for examples, treating the same tumor with multiple drugs and drug combinations can be exploited for detailed mechanistic study that cannot be readily preformed in human patients;
    Studying the tumor microbiome: bacteria, viruses or fungi that might be present in cancer tumors.
2. Testing the effect of novel drugs or drug combinations on tumor slices in order to prioritize drugs or drugs combinations for further drug development as well as mechanistic studies, pre-clinical in-vivo testing and clinical trials.
3. Predicting patient's response to drugs (e.g. anti-cancer drugs) and drug combinations and consequently using this prediction to tailor the specific treatment regime for the patient (i.e. personalized medicine).
4. As the tissue slice maintains the structure and presents high viability following 5 days of culture, this system allows modeling of chronic as well as acute toxicity studies, including the metabolic activity of the tissue.
5. A culture presenting positive ex-vivo response can be used as a criterion for inclusion of a patient in a clinical trial. This step can thus pre-select patients with high a chance of response and consequently can improve the chance of successful clinical trials. In such cases the ex-vivo tissue culture might later become part of the criteria for drug eligibility. Thus, according to specific embodiments the culture system comprises a drug.

According to other specific embodiments, the method of the present invention described hereinabove comprises adding a drug or a drug combination, as further described herein below.

As used herein, the phrase "drug" refers to an agent that has an anti-pathologic effect including small molecules and biological drugs (e.g. nucleic acid agents, polypeptides, antibodies, aptamers etc.). Typically, the drug is exogenous to the precision-cut tissue slice or in the human body or tissue from which the precision cut tissue slice is derived. The drug may be a drug approved by the regulatory agencies for the treatment of the pathology, or an under-development drug. According to specific embodiments, the drug is a batch of a drug.

According to specific embodiments, the drug is an anti-inflammatory drug.

Non-limiting examples of anti-inflammatory drugs that can be used with specific embodiments of the invention include: Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpip alone; Fentiazac; Flazalone; Fluazacort; Flufenamic Acid; Flumizole; Flunisolide Acetate; Flunixin; Flunixin Meglumine; Fluocortin Butyl;

Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

According to other specific embodiments, the drug is an anti-cancer drug.

As used herein, the phrase "anti-cancer drug" refers to an agent that has an anti-tumor effect including chemotherapy, small molecules, biological drugs, hormonal therapy, antibodies and targeted therapy.

Anti-cancer drugs that can be used with specific embodiments of the invention include, but are not limited to: Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

Non-limiting examples for anti-cancer approved drugs include: abarelix, aldesleukin, aldesleukin, alemtuzumab, alitretinoin, allopurinol, altretamine, amifostine, anastrozole, arsenic trioxide, asparaginase, azacitidine, AZD9291, AZD4547, AZD2281, bevacuzimab, bexarotene, bleomycin, bortezomib, busulfan, calusterone, capecitabine, carboplatin, carmustine, celecoxib, cetuximab, cisplatin, cladribine, clofarabine, cyclophosphamide, cytarabine, dabrafenib, dacarbazine, dactinomycin, actinomycin D, Darbepoetin alfa, Darbepoetin alfa, daunorubicin liposomal, daunorubicin, decitabine, Denileukin diftitox, dexrazoxane, dexrazoxane, docetaxel, doxorubicin, dromostanolone propionate, Elliott's B Solution, epirubicin, Epoetin alfa, erlotinib, estramustine, etoposide, exemestane, Filgrastim, floxuridine, fludarabine, fluorouracil 5-FU, fulvestrant, gefitinib, gemcitabine, gemtuzumab ozogamicin, goserelin acetate, histrelin acetate, hydroxyurea, Ibritumomab Tiuxetan, idarubicin, ifosfamide, imatinib mesylate, interferon alfa 2a, Interferon alfa-2b, irinotecan, lenalidomide, letrozole, leucovorin, Leuprolide Acetate, levamisole, lomustine, CCNU, meclorethamine, nitrogen mustard, megestrol acetate, melphalan, L-PAM, mercaptopurine 6-MP, mesna, methotrexate, mitomycin C, mitotane, mitoxantrone, nandrolone phenpropionate, nelarabine, Nofetumomab, Oprelvekin, Oprelvekin, oxaliplatin, paclitaxel, palbociclib palifermin, pamidronate, pegademase, pegaspargase, Pegfilgrastim, pemetrexed disodium, pentostatin, pipobroman, plicamycin mithramycin, porfimer sodium, procarbazine, quinacrine, Rasburicase, Rituximab, sargramostim, sorafenib, streptozocin, sunitinib maleate, tamoxifen, temozolomide, teniposide VM-26, testolactone, thioguanine 6-TG, thiotepa, thiotepa, topotecan, toremifene, Tositumomab, Trametinib, Trastuzumab, tretinoin ATRA, Uracil Mustard, valrubicin, vinblastine, vinorelbine, zoledronate and zoledronic acid.

According to specific embodiments, the anti-cancer drug is selected from the group consisting of Gefitinib, Lapatinib, Afatinib, BGJ398, CH5183284, Linsitinib, PHA665752, Crizotinib, Sunitinib, Pazopanib, Imatinib, Ruxolitinib, Dasatinib, BEZ235, Pictilisib, Everolimus, MK-2206, Trametinib/AZD6244, Vemurafinib/Dabrafenib, CCT196969/CCT241161, Barasertib, VX-680, Nutlin3, Palbociclib, BI 2536, Bardoxolone, Vorinostat, Navitoclax (ABT263), Bortezomib, Vismodegib, Olaparib (AZD2281), Simvastatin, 5-Fluorouricil, Irinotecan, Epirubicin, Cisplatin and Oxaliplatin.

According to specific embodiments, the anti-cancer drug is selected from the group consisting of 4-hydroperoxy cyclophosphamide, 5-5-fluorouracil (5FU), oxaliplatin, irinotecan, docetaxel, cisplatin, trametinib, palbociclib and AZD4547.

According to specific embodiments, the anti-cancer drug is selected from the group consisting of 5-fluorouracil (5FU), oxaliplatin, irinotecan, cisplatin, 4-hydroperoxy cyclophosphamide, docetaxel, doxorubicin, navalbine, gemcitabine, gefitinib, tamoxifen, olaparib, trametinib, everolimus and palbociclib.

It will be appreciated that the culture system and methods described herein can be used to test the differential effect of drug combinations.

Thus, according to specific embodiments, the drug is a drug combination.

Specific concentrations of the drug in the culture system and methods of the present invention can be derived by culturing different drug concentrations on several cancer tissues (of the same or different type) and assessing the range where a dose dependent response is achieved. Typically, this dose dependent range reflects the spectrum whereby the cultured cancer tissue is expected to respond or show no response, yielding a predictive result.

According to specific embodiments, the drug concentration in the culture system and methods of the present invention is at least the same as the drug IC50 dose in a cell line (e.g., a cell line of the same tissue type and/or species).

According to specific embodiments, the drug concentration in the culture system and methods of the present invention is higher than the drug IC50 dose in a cell line (e.g., a cell line of the same tissue type and/or species).

According to specific embodiments, the drug concentration in the culture system and methods of the present invention is at least 2 fold, at least 3 fold, at least 5 fold, at least 10 fold, at least 25 fold, at least 50 fold, at least 100 fold the drug IC50 dose in a cell line (e.g., a cell line of the same tissue type and/or species).

According to specific embodiments, the drug concentration in the culture system and methods of the present invention is at least 10 fold the drug IC50 dose in a cell line (e.g., a cell line of the same tissue type and/or species).

Specific concentrations of anti-cancer drugs that can be used with some embodiments of the present invention are shown in Tables 5-6 herein below.

TABLE 5

Specific anti-cancer drug concentration ranges

| Drug | Concentration Range |
|---|---|
| 5-FU | 40-80 uM |
| Oxaliplatin | 16-32 uM |
| Irinotecan | 20-96 uM |
| Cisplatin | 10-30 uM |
| 4-hydroxycyclophosphamide | 2-20 uM |
| Docetaxel | 20-40 uM |
| Doxorubicin | 5-40 uM |
| Navalbine | 5-10 uM |
| Gemcitabine | 5-50 uM |
| Gefitinib | 1-10 uM |

TABLE 5-continued

Specific anti-cancer drug concentration ranges

| Drug | Concentration Range |
|---|---|
| Tamoxifen | 10-20 uM |
| Olaparib | 10-40 uM |
| Trametinib | 1-10 uM |
| Everolimus | 2-10 uM |
| Palbociclib | 2.5-10 uM |

TABLE 6

Specific anti-cancer drugs concentrations

| Drug | Concentration |
|---|---|
| 5-FU | 80 uM |
| Oxaliplatin | 10 uM |
| Irinotecan | 30 uM |
| Cisplatin | 20 uM |
| 4-hydroxycyclophosphamide | 10 uM |
| Docetaxel | 20 uM |
| Doxorubicin | 5 uM |
| Tamoxifen | 10 uM |
| Olaparib | 20 uM |
| Trametinib | 1 uM |
| Gemcitabine | 5 uM |

According to specific embodiments, several tissue slices from one tissue are prepared and cultured in several culture vessels (e.g. wells of a plate) allowing testing of a number of drugs and drug combinations.

According to specific embodiments, the methods of the invention comprise:
  (i) determining the effect of a plurality (e.g., at least 2) of drugs according to the method of the present invention; and
  (ii) determining the effect of combinations of drugs shown to be efficacious according to step (i), wherein increased sensitivity of the tissue to a drug combination indicates efficacy of the drug combination.

As used herein, the term "increased sensitivity" refers to an increase in the effect induced by the drug combination in comparison to the effect induced by each of the drugs in the combination, which may by an additive effect or a synergistic effect. According to specific embodiments, the effect is a synergistic effect.

According to specific embodiments the increase is at least 1.5 fold, at least 2 fold, at least 3 fold, at least 5 fold, at least 10 fold, or at least 20 fold as compared to the effect induced by each of the drugs in the combination.

According to other specific embodiments the increase is by at least 5%, by at least a 10%, at least 20%, at least 30%, at least 40%, at least 50%, at least 60%, at least 70%, at least 80%, at least 90% or more than 100% as compared to the effect induced by each of the drugs in the combination.

As mentioned, according to specific embodiments, the tissue or the tissue slices may be stored i.e. at 4° C. or cryopreserved and thawed as desired allowing serial testing of several drugs and drugs combinations sequentially.

Thus, for example, according to specific embodiments, the methods of the invention comprise:
  (i) determining the effect of at least two drugs according to the method of the invention;
  (ii) culturing an additional tissue slice obtained from the pathological tissue obtained from the subject (e.g. following cryopreservation and thawing) according to the method of the present invention;

(iii) adding combinations of drugs determined to be efficacious for the treatment of the disease in the subject according to step (i); and (iv) determining the effect of the combination of drugs on the tissue slice, wherein increased sensitivity of the tissue slice to the combination of drugs indicates efficacy of the combination of drugs for the treatment of the disease in the subject.

The drug or the drug combination may be added to the culture at various time points. According to specific embodiments, the drug is added to the culture 2-48 hours, 2-36, 2-24, 12-48, 12-36 or 12-24 hours following the beginning of the culture.

According to a specific embodiment, the drug or the drug combination is added to the culture 12-24 hours following the beginning of the culture.

According to a specific embodiment, the drug or the drug combination is added to the culture 12-36 hours following the beginning of the culture.

According to a specific embodiment, the drug or the drug combination is added to the culture 12-48 hours following the beginning of the culture.

Culturing in the presence of the drug or the drug combination may be effected throughout the whole culturing period from first drug addition or can be limited in time. Alternatively, or additionally, the drug or the drug combination may be added to the culture multiple times e.g. when the culture medium is refreshed.

Selection of drug concentration and incubation time with the drug or the drug combination are well within the capability of those skilled in the art.

According to specific embodiments, the drug concentration and incubation time with the drug or the drug combination results in detectable effect on the tissue as further described hereinbelow.

Selection of drug concentration used for the ex-vivo testing that will result in detectable effect on the tissue is well within the capabilities of skilled in the art. Preferably, the concentration used should be within the linear range of the selected parameter.

The number of tested drug concentration can be at least 1, at least 2, at least 3, at least 5, at least 6, 1-10, 2-10, 3-10, 5-10, 1-5, 2-5 and 3-5 different concentrations in the same assay.

The number of samples repeats for each of the tested drug concentration can be 2, 3, 4, 5 or 6 repeats.

Following culturing the effect of the drug or the drug combination on the tissue can be determined to thereby determine efficacy of a drug.

Thus, according to another aspect of the present invention there is a method of determining efficacy of a drug or a batch of a drug, the method comprising:

(i) culturing a precision-cut tissue slice on a tissue culture insert in culture medium under a highly oxygenated atmosphere containing at least 50% oxygen; and agitating the culture in a rotation facilitating intermittent submersion of said tissue slice in said culture medium;

(ii) adding the drug or the batch of a drug to said culture medium; and (iii) determining the effect of said drug or said batch of a drug on said tissue, wherein sensitivity of said tissue to said drug indicates efficacy of said drug.

According to specific embodiments, the determining step is effected following pre-determined culturing time. The culturing time may vary and determination of the culturing time that will result in detectable effect is well within the capabilities of those skilled in the art.

According to specific embodiments, the determining is effected within 2-10, 2-7, 2-5, 3-10, 3-7, 3-5 or 4-5 days of culturing.

According to a specific embodiment, the determining is effected within 3-5 days of culturing.

According to another specific embodiment, the determining is effected within 4-5 days of culturing.

Methods of determining effects induced by the drug or the drug combination are known in the art and include for example:

Viability evaluation using e.g. the MTT test which is based on the selective ability of living cells to reduce the yellow salt MTT (3-(4, 5-dimethylthiazolyl-2)-2, 5-diphenyltetrazolium bromide) (Sigma, Aldrich St Louis, MO, USA) to a purple-blue insoluble formazan precipitate; the WST assay or the ATP uptake assay;

Proliferation evaluation using e.g. the BrDu assay [Cell Proliferation ELISA BrdU colorimetric kit (Roche, Mannheim, Germany] or Ki67 staining;

Cell death evaluation using e.g. the TUNEL assay [Roche, Mannheim, Germany] the Annexin V assay [Apo-Alert® Annexin V Apoptosis Kit (Clontech Laboratories, Inc., CA, USA)], the LDH assay, the Activated Caspase 3 assay, the Activated Caspase 8 assay and the Nitric Oxide Synthase assay;

Senescence evaluation using e.g. the Senescence associated-β-galactosidase assay (Dimri G P, Lee X, et al. 1995. A biomarker that identifies senescent human cells in culture and in aging skin in vivo. Proc Natl Acad Sci USA 92:9363-9367) and telomerase shortening assay;

Cell metabolism evaluation using e.g. the glucose uptake assay;

Various RNA and protein detection methods (which detect level of expression and/or activity); and Morphology evaluation using e.g. the Haemaotxylin & Eosin (H&E) staining;

According to specific embodiments, the determining is effected by morphology evaluation, viability evaluation, proliferation evaluation and/or cell death evaluation.

According to specific embodiments, the determining is effected by morphology evaluation.

Morphology evaluation using H&E staining can provide details on e.g. cell content, size and density, ratio of viable cells/dead cells, ratio of diseased (e.g. tumor) cells/healthy cells, immune cells infiltration, fibrosis, nuclear size and density and integrity, apoptotic bodies and mitotic figures. According to specific embodiments effect of the drug on the tissue is determined by morphology evaluation by e.g. a pathologist.

Typically, results from each of the assays are expressed in a numeric form wherein a high score correlates with drug sensitivity and a low score correlated with drug resistance.

As used herein the phrase "sensitivity to a drug" or "sensitivity to drug combination" refers to the ability of a drug or drug combination to induce cellular changes such as changes in cell viability, proliferation rate, differentiation, cell death, necrosis, apoptosis, senescence, transcription and/or translation rate of specific genes and/or changes in protein states e.g. phosphorylation, dephosphorylation, translocation and any combinations thereof. According to specific embodiments, the cellular changes are reflected by decreased cell viability, decreased proliferation rate, increased cell death and/or aberrant morphology as compared to same in the absence of the drug.

According to a specific embodiment the cellular changes are reflected by decreased cell viability.

According to a specific embodiment the cellular changes are reflected by aberrant morphology.

According to specific embodiments the change is at least 1.5 fold, at least 2 fold, at least 3 fold, at least 5 fold, at least 10 fold, or at least 20 fold as compared to same in the absence of the drug.

According to other specific embodiments the change is by at least 5%, by at least a 10%, at least 20%, at least 30%, at least 40%, at least 50%, at least 60%, at least 70%, at least 80%, at least 90%, at least 95%, at least 99% or at least 100% as compared to same in the absence of the drug.

According to specific embodiments, the determined efficacy of the drug indicates the potency of a batch of a drug, that is, drug sensitivity is indicative that the batch is potent.

As used herein, the term "potency" refers to the measure of the biological activity of the drug, based on the attribute of the drug which is linked to the relevant biological properties (i.e.; drug sensitivity).

According to specific embodiments of the invention, the method comprising comparing the sensitivity of the tissue to the drug with sensitivity of the tissue to a reference standard batch of the drug, so as to determine the relative potency of the batch.

As used herein, the term "relative potency" refers to a qualitative measure of potency of a batch of the drug, relatively to a standard reference (RS) of the drug, having a known potency.

According to specific embodiments the potency of a batch of the drug, is determined relatively to the known potency of a reference standard (RS).

As used herein, the phrase "reference standard" or "RS" refers to a standardized drug, which is used as a measurement base for the drug. RS provides a calibrated level of biological effect against which new preparations of the drug can be compared to.

According to a specific embodiment, the RS is characterized by optimum potency and quality of an active component that is effective in treating the disease (e.g., inflammatory disease, cancer).

Calculating potency and relative potency are known in the art. According to specific embodiments the relative potency is calculated using a software suitable for biological assays, such as parallel line analysis software e.g., PLA (Stegmann Systems GmbH) and Gen5 data analysis software (BioTek).

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

According to specific embodiments, the determined efficacy of the drug or the drug combination indicates suitability of the drug for the treatment of a disease.

As the present inventors show that the developed EVOC system can predict responses of tumors to anti-cancer drugs and combinational treatment (Example 2 in the Examples section which follows), the present invention also contemplates the use of the culture systems and methods described herein for predicting response of a specific subject to a treatment regime, thereby selecting the suitable treatment regime for this specific subject and treating the subject according to this selection.

Thus, according to an aspect of the present invention there is provided a method of selecting a drug for the treatment of a disease in a subject in need thereof, the method comprising:
(i) culturing a pathological tissue precision-cut tissue slice obtained from the subject on a tissue culture insert in culture medium under a highly oxygenated atmosphere containing at least 50% oxygen; and agitating the culture in a rotation facilitating intermittent submersion of said tissue slice in said culture medium;
(ii) adding the drug to said culture medium; and
(iii) determining the effect of said drug on said tissue, wherein sensitivity of said tissue to said drug indicates efficacy of said drug for the treatment of said disease in said subject.

According to another aspect of the present invention there is provided a method of treating a disease in a subject in need thereof, the method comprising:
(a) selecting a drug or a combination of drugs according to the method described herein; and
(b) administering to said subject a therapeutically effective amount of a drug or a combination of drugs demonstrating efficacy for the treatment of said disease in said subject, thereby treating the disease in the subject.

As used herein the phrase "subject" refers to a mammalian subject (e.g., human being) who is diagnosed with the disease or is at risk of to develop a disease. Veterinary uses are also contemplated. The subject may be of any gender and any age including neonatal, infant, juvenile, adolescent, adult and elderly adult.

The term "treating" refers to inhibiting or arresting the development of a pathology (disease, disorder, or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

Determination of a therapeutically effective amount of a drug or a drug combination is well within the capability of those skilled in the art. The dosage may vary depending upon the drug chosen, the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

According to specific embodiments, the disease is an inflammatory disease which can be chronic inflammatory disease of acute inflammatory disease.

Inflammatory Diseases Associated with Hypersensitivity

Non-Limiting Examples of Hypersensitivity Include:

Type II hypersensitivity including, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl: S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Internet (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595);

Type IV or T cell mediated hypersensitivity, including, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6): 893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus;

Delayed type hypersensitivity including, but are not limited to, contact dermatitis and drug eruption.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Internet (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

According to specific embodiments, the disease is cancer.

The terms "cancer" and "cancerous" describe the physiological condition in mammals that is typically characterized by unregulated cell growth. As used herein, the terms "cancer" and "cancerous" refers to any solid tumor, cancer metastasis and/or a solid pre-cancer.

Examples of cancer include but are not limited to, carcinoma, blastoma, sarcoma and lymphoma. More particular examples of such cancers include squamous cell cancer, lung cancer (including small-cell lung cancer, non-small-cell lung cancer, adenocarcinoma of the lung, and squamous carcinoma of the lung), glioma, melanoma cancer, cancer of the peritoneum, hepatocellular cancer, gastric, gastro esophageal or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, soft tissue sarcoma, kidney or renal cancer, prostate cancer, vulval cancer, thyroid cancer, hepatic carcinoma, Kaposi's sarcoma carcinoid carcinoma, and various types of head and neck cancer.

Precancers are well characterized and known in the art (refer, for example, to Berman J J. and Henson D E., 2003. Classifying the precancers: a metadata approach. BMC Med Inform Decis Mak. 3:8). Examples of precancers include but are not limited to include acquired small precancers, acquired large lesions with nuclear atypia, precursor lesions occurring with inherited hyperplastic syndromes that progress to cancer, and acquired diffuse hyperplasias and diffuse metaplasias. Non-limiting examples of small precancers include HGSIL (High grade squamous intraepithelial lesion of uterine cervix), AIN (anal intraepithelial neoplasia), dysplasia of vocal cord, aberrant crypts (of colon), PIN (prostatic intraepithelial neoplasia).

Non-limiting examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Non-limiting examples of precursor lesions occurring with inherited hyperplastic syndromes that progress to cancer include atypical mole syndrome, C cell adenomatosis and MEA. Non-limiting examples of acquired diffuse hyperplasias and diffuse metaplasias include Paget's disease of bone and ulcerative colitis.

According to specific embodiments, the cancer is selected from the group consisting of ovarian cancer, colorectal cancer, lung cancer, pancreatic cancer, gastric cancer, gastro esophageal cancer and breast cancer.

According to specific embodiments, the cancer is a metastatic cancer.

As various additional technologies are available to predict a patient's response to a treatment regime, the methods of the present invention can be combined with other methods known in the art, such as, but not limited to genetic profiling, tumor derived cell lines generated from patients' tumors and patient-derived xenograft (PDX) models as also described in the Examples section that follows.

According to specific embodiments, the method is effected in combination with genetic profiling.

As used herein, the term "genetic profiling" refers to the molecular signature of a set of genes in a biological samples using any suitable profiling technology, such as, but not limited to, DNA sequencing, RNA sequencing and microarray techniques.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Tissue Slices—

Healthy and cancerous tissues (liver, lung, colon, breast, pancreas or metastatic tissues of cancer originating from lung, colon, breast or pancreas) were obtained from mice PDX models (Nod Scid Gamma Mice Jackson Laboratories USA and/or Harlan Laboratories); human biopsies and surgically removed tissues; and human derived xenografts (ovarian cancer, Pancreatic PDX). Following harvesting, the fresh tissue was immediately placed in ice-cold Phosphate-buffered saline (PBS, Biological Industries, Kibbutz Beit Haemek, Israel) or ice-cold culture medium (RPMI Biological Industries). A precision tissue slicer (Compresstome™ VF-300: Precisionary Instruments Inc. NC, USA) was cleaned with 70% ethanol, rinsed twice with sterile water and a new blade (Double Edge Blades 32017759 Belgar, Jerusalem, Israel) was attached and positioned in place.

The tissue remained on ice until transferred to the pre-cleaned tissue slicer; then the tissue was removed from the PBS and gently attached to the plunger with contact glue and stabilized in 3% low gel agarose warmed to 50° C. and then cooled to solidify before use (agarose, low gelling A0701 Sigma-Aldrich, 3% in 0.9 g NaCl). The plunger with the tissue was inserted to its designated place in the tissue slicer and the bath was filled with ice-cold Williams Medium E with added penicillin and streptomycin. To maintain the medium in the bath at low temperatures, a hollow cooling coil that sits in the bath was constructed. Ice cold water was then pumped through the coil using a standard immersion pump. The tissue was sliced to ~250 μM slices. Approximately 30-40 slices were prepared from a 1 $cm^3$ piece of tissue. Two or three slices were immediately placed in disposable plastic histology cassettes and fixed in 4% PFA.

Culturing Procedure—

Tissue slices were placed individually in 6-wells plates (Corning CC-3516 Getter, Petach-Tikva, Israel) directly, on top of titanium inserts (MA0036 Well Inserts, Alabama R&D, Alabama, USA) or on PEG or PEG placed on a titanium insert. Each well contained 4.5 ml of DMEM/F12 or M199 medium supplemented with penicillin (100 IU/ml), streptomycin (100 μg/ml), gentamycin (G1397 50 μg/ml Sigma-Aldrich), 5% Fetal Calf Serum (FCS, 10270106 Gibco Sigma-Aldrich, Rehovot, Israel), amphotericin B (A-4888 2.5 μg/ml Sigma-Aldrich) and glutamine (L-Glutamine 03-020-1B 100 μl/ml Biological Industries). The plates were incubated in a humidified incubator at 37° C. with 5% $CO_2$ and 21% or 80% $O_2$ (using the oxygen Chamber: BioSpherix C274, NY, USA; oxygen Controller: Biospherix ProOx C21, NY, USA; and oxygen 98% Maxima Air Innovations, Ashdod, Israel).

The entire incubator was put on an orbital shaker agitating (TOU-120N MRC, Holon, Israel) at 70 rpm. Following overnight incubation, the medium was replaced with fresh medium. In the indicated wells the fresh medium contained an anti-cancer drug [4-hydroperoxy cyclophosphamide (sc-206885 ENCO, Petach Tikva, Israel), 5-fluorouracil (5FU, A10042 Adooq Biotag, Kfar Yona, Israel), oxaliplatin (O9512 Sigma-Aldrich), irinotecan (A10479-200 Adooq Biotag, Kfar Yona, Israel), docetaxel (01885 Sigma-Aldrich), cisplatin (Sigma-Aldrich), trametinib (A11029 Adooq Biotag, Kfar Yona, Israel), CDK4/6 inhibitor palbociclib (PZ0199 Sigma-Aldrich) or FGFR inhibitor AZD4547 (A11075-5 Adooq Biotag) at the indicated concentrations. The medium was replaced once every 48 hours with fresh drug/DMSO for 4-6 days.

Functional Assays—

Eighteen to twenty-four hours prior to the end of culturing, BrdU was added to the medium (Final concentration: 10 μm/ml) for subsequent staining with an anti-BrdU antibody (BRDU+anti-BRDU B5002 Sigma-Aldrich and 94-MS-1058-P Eldan, Petach Tikva, Israel) and/or anti Ki67 (94-RM-9106-S Eldan, Petach Tikva, Israel). At the end of culturing, the tissues were placed between two glass coverslips, placed in a disposable plastic histology cassette and fixed overnight in 4% Paraformalydehyde (PFA). Following the slices were paraffinized, blocked and cut to 5 μM slices for Hematoxylin & Eosin (H&E) staining and other IHC staining such as Ki67 staining.

Example 1

Ex-Vivo Organ Culture Conditions for Maintaining Structure and Function of Healthy and Tumor Tissue Slices In order to obtain tissue structure and function for at least 5 days in an ex-vivo organ culture (EVOC) several conditions were examined. The conditions included:

1. culturing the tissue slices on different surfaces, such as titanium inserts, as compared to directly immersing the slices in the culture medium;
2. incubating the tissue under standard tissue culture conditions of 21% $O_2$ and 5% $CO_2$ as compared to highly oxygenated atmosphere containing 80% $O_2$;
3. culturing 1 slice in each well as compared to several slices in each well;
4. using different media such as DMEM/F12 and M199;
5. culturing on PEG with or without titanium inserts.

The results are summarized in Table 1 below.

To this end, incubating the tissue under highly oxygenated atmosphere containing 80% $O_2$ significantly increased tissue viability as compared to standard tissue culture conditions of 21% $O_2$ (representative culture of human ovarian cancer derived xenografts is shown in FIG. 1). In addition, the tissue survives better when supported on titanium inserts that allow for a medium/air interface as compared to directly inserting the tissue to the tissue culture well such that the slice is completely immersed in medium (representative culture of human ovarian cancer derived xenografts is shown in FIG. 1). Furthermore, DMEM/F12 was a better medium than M199 (representative culture of human ovarian cancer derived xenografts is shown in FIG. 2).

tissues were examined by a pathologist and were considered fully viable with the same morphology as regular pathology tissue from the patient.

Taken together, culturing one tissue slice directly in the middle of a titanium insert in DMEM/F12 medium under highly oxygenated atmosphere containing 80% $O_2$ and agitating the culture at orbital shaking which facilitates intermittent submersion of the tissue slice in the culture medium maintained the structure and viability of the tissue for at least 5 days of culture. This newly developed EVOC system was used in the following Examples hereinbelow.

Example 2

The Developed EVOC can be Used for Predicting Response of Tumors to Anti-Cancer Drugs The developed EVOC can predict the in-vivo response of patient-derived xenografts to treatment: Several mouse patient-derived xenograft (PDX) models with known in-vivo responses to anti-cancer drugs were purchased from Jackson Laboratories. The tumors were excised from the mice, cultured as described in the Materials and Methods and Example 1 hereinabove and the sensitivity of the tissue

TABLE 1

Summary of human tissue ex-vivo organ culture (EVOC) under different culturing conditions

| Tissue | Tissue culture Insert | $O_2$% | Culture Medium | Days in Culture | Viability* |
|---|---|---|---|---|---|
| Ovarian Cancer (PDX model) | titanium | 21% | DMEM/F12 | 5 | 5% |
|  | no insert | 21% | DMEM/F12 | 5 | 0% |
|  | titanium | 80% | DMEM/F12 | 5 | 80% |
|  | no insert | 80% | DMEM/F12 | 5 | 50% |
|  | titanium | 80% | M199 | 5 | 20% |
| Breast Cancer (PDX model) | titanium | 80% | DMEM/F12 | 5 | 60-90% |
|  | no insert | 80% | DMEM/F12 | 5 | 0-40% |
|  | titanium | 80% | DMEM/F12 | 5 | 90%+ |
|  | titanium with PEG | 80% | DMEM/F12 | 5 | 0-5% |
| Colon Cancer (PDX model) | titanium | 80% | DMEM/F12 | 5 | 100% |
|  | titanium with PEG | 80% | DMEM/F12 | 5 | 5% |
| Lung Cancer (PDX model) | titanium | 80% | DMEM/F12 | 5 | 100% |
| Pancreatic Cancer (PDX model) | titanium | 80% | DMEM/F12 | 5 | 90% |
| CRC Primary** | titanium | 80% | DMEM/F12 | 4 | 100% |
| CRC Liver Metastasis** | titanium | 80% | DMEM/F12 | 4 | 100% |
| CRC Peritoneal Metastasis | titanium | 80% | DMEM/F12 | 5 | 80-100% |
| Lung Primary** | titanium | 80% | DMEM/F12 | 5-7 days | 100% |

*Experiments are in duplicate or triplicate to improve the robustness of the assay. % Viability is subjective evaluation by morphological analysis of the area of optimal viability taken independently by at least two different independent observers.
**Tissue was obtained from surgery and directly cultured.
*** PDX—patient-derived xenograft, CRC—colorectal carcinoma The tissues for the EVOCs presented in Table 1 above were all obtained from surgery. However, the developed assay can be adapted for small biopsy tissue taken by core biopsy from the tumor tissue (FIG. 9). Specifically, the tissue is embedded in agarose in two steps: first liquid agarose is placed in a small metal tray, the core biopsies placed on the agarose and agarose added on top of the biopsies. The tray is cooled and the agarose with the biopsies is cut out en-bloc. In the second step, the block of agarose is fixed to the plunger with contact clue and surrounded by agarose in a manner similar to that used for tissue pieces.

Overall, EVOCs from different sources representing numerous tissues which maintained the structure and the viability of the tissue for at least 5 days of culture were established (FIGS. 1, 2 and 11). Importantly, all of the slices to anti-cancer agents were tested. Altogether, seven PDX models originating from 3 tumor types (breast cancer, lung cancer and colorectal cancer) were tested and in all tested models the developed EVOC system was able to correctly predict sensitivity of the tumors to the drug treatment (Table 2 below and FIGS. 3-4). Additionally a clear dose dependent response in the EVOC system was observed.

Thus, as can be seen in FIGS. 3-4 and Table 2 below, tumors that were resistant to treatment in-vivo were also resistant to treatment ex-vivo, even when very high doses were applied. On the contrary, applying a treatment which the tumors were sensitive to in-vivo, cell death was detected ex-vivo at low drug concentrations and drug sensitivity increased with increased drug concentrations.

TABLE 2

The in-vivo response of PDX mice models to systemic drug treatment as compared to the response of the same tumors ex-vivo.

| Model # | Cancer type | Drug & EVOC Dose (mM) | In-vivo | EVOC |
|---|---|---|---|---|
| TM00356 | Lung | Docetaxel (80 μM) | PR | PR |
| | | Cisplatin (30 μM) | NR | NR |
| | | Trametinib (1 μM) | NR | NR |
| TM00213 | Lung | Docetaxel (80 μM) | CR | CR |
| | | Cisplatin (30 μM) | PR | PR |
| | | Trametinib (1 μM) | PR | PR |
| TM00096 | Breast | Docetaxel (60 μM) | CR | CR |
| | | 4-HA (60 μm) | PR | PR |
| TM00098 | Breast | Docetaxel (60 μM) | CR | CR |
| | | 4-HA (60 μM) | CR | CR |
| TM00164 | Colon | 5-FU (320 μM) | PR | PR |
| | | Oxaliplatin (16 μM) | CR | PR |
| TM00134 | Colon | 5-FU (320 μM) | NR | NR |
| | | Oxaliplatin (16 μM) | NR | NR |
| | | 5-FU (20 μM) + Oxaliplatin (4 μM) | | NR |
| TM00170 | Colon | 5-FU (320 μM) | PR | PR |
| | | Oxaliplatin (16 μM) | PR | PR |
| | | 5-FU (20 μM) + Oxaliplatin (4 μM) | | PR |

*In vivo data was generated by Jackson Laboratories.
*5-FU—5-Fluorouricil; 4-HA—4 Hydroperoxy cyclophosphamide; CR—complete response; PR—partial response; and NR—No response.

The developed EVOC demonstrates that human tumors present differential sensitivity to different anti-cancer treatments: Patient tumor tissues excised from patient tumors during surgical excision were directly cultured as described in the Materials and Methods and Example 1 hereinabove and the sensitivity of the tissue slices to anti-cancer agents was tested. The most common anti-cancer regimens were used for each tumor type, that is, for example, for human colorectal cancer the standard treatment is 5-fluorouracil, oxaliplatin and/or irinotecan. FIG. 5 demonstrates an example for a tumor that was found to be resistant to high dose of 5-fluorouracil but relatively sensitive to irinotecan and oxaliplatin. Determining cell proliferation by e.g. Ki67 staining can also be used to evaluate tissue slice viability and sensitivity to anti-cancer agents. Thus, FIG. 8 demonstrates an example for a colorectal cancer that was found to be partially sensitive to 5-fluorouracil but very sensitive to oxaliplatin treatment by Ki67 staining.

Taken together, the developed EVOC system clearly indicated that patient tumors can be sensitive to one anti-cancer drug, but resistant to another. Moreover, EVOC generated from different individual patients responded differentially to the same anti-cancer treatments (FIG. 6 and Tables 3-4 below). In addition, for each anti-cancer treatment a dose dependent response was observed (e.g. Tables 3-4).

TABLE 3

The ex-vivo response of Human colorectal cancer obtained from 8 patients.

| Drug | Dose | EVOC 3 | EVOC 5 | EVOC 6 | EVOC 1 | EVOC 8 | EVOC 9 | EVOC 11 | EVOC 7 |
|---|---|---|---|---|---|---|---|---|---|
| Immediate | | 4 | 4 | 4 | 4 | 4 | 4 | 4 | 4 |
| DMSO | | 4 | 4 | 3 | 3 | 4 | 3 | 4 | 4 |
| Irinotecan | 32 μM | | 3 | 2 | | 3 | 4 | 1 | 3 |
| | 64 μM | 4 | 3 | 1 | 3 | | | | 3 |
| | 128 μM | | 2 | 1 | 2 | 1 | 0 | 0 | 3 |
| 5-FU | 20 μM | 3 | 4 | 2 | | | | | 3 |
| | 80 μM | 2 | 4 | 2 | 2 | 4 | 4 | 0 | 3 |
| | 320 μM | 0 | 3 | 2 | 1 | 4 | 0 | 1 | 3 |
| Oxaliplatin | 16 μM | 4 | 4 | 2 | | 4 | 4 | 0 | 4 |
| | 32 μM | | 2 | 1 | 2 | | | | 2 |
| | 64 μM | 2 | 0 | 1 | 2 | 1 | 0 | 0 | 2 |

0-Complete response; 1-strong partial response; 2-medium partial response; 3-weak partial response; and 4-No response.

TABLE 4

The ex-vivo response of Human colorectal cancer for combination therapy.

| | DMSO | 5-FU & Oxaliplatin | | | | | 5-FU & Irinotecan | | 5-FU & Irinotecan & Oxaliplatin 20 μM & 4 μM | | |
|---|---|---|---|---|---|---|---|---|---|---|---|
| | | 2 μM & 2 μM | 20 μM & 4 μM | 20 μM & 20 μM | 80 μM & 20 μM | 320 μM & 64 μM | 20 μM & 30 μM | 80 μM & 16 μM | | 80 μM & 64 μM & 32 μM | 320 μM & 128 μM & 64 μM |
| EVOC3 | 4 | 4 | | | | | | | 3 | 4 | |
| EVOC5 | 4 | | | | | | | | 4 | 0 | 0 |
| EVOC6 | 3 | | | | | | | | | 2 | 0 |
| IchEVOC1 | 3 | | | | | | | | | 2 | |
| EVOC9 | 3 | | | | | | | | | | 0 |
| EVOC11 | 4 | | | | 2 | 0 | | | | | 0 |
| EVOC7 | 4 | | | | 4 | 2 | | | | | |
| EVOC20 | 4 | | 2 | | | | 2 | | | | |

TABLE 4-continued

The ex-vivo response of Human colorectal cancer for combination therapy.

| | | 5-FU & Oxaliplatin | | | | | 5-FU & Irinotecan | | 5-FU & Irinotecan & Oxaliplatin 20 μM | | |
|---|---|---|---|---|---|---|---|---|---|---|---|
| | DMSO | 2 μM & 2 μM | 20 μM & 4 μM | 20 μM & 20 μM | 80 μM & 20 μM | 320 μM & 64 μM | 20 μM & 30 μM | 80 μM & 16 μM | & 4 μM & 4 μM | 80 μM & 64 μM & 32 μM | 320 μM & 128 μM & 64 μM |
| EVOC23 | 4 | | | | | | 4 | | | | |
| EVOC24 | 4 | | 1 | | | | 3 | | | | |
| EVOC26 | 4 | | 3 | | | | 3 | | | | |
| EVOC28 | 4 | | 3 | | | | 2 | | | | |
| EVOC29 | 4 | | | | | | 2 | | | | |
| EVOC33 | 3 | | 3 | | | | | | | | |
| EVOC34 | 4 | | 4 | | | | | | | | |
| EVOC35 | 4 | | 4 | | | | 4 | | | | |
| EVOC36 | 4 | | 4 | | | | 4 | | | | |
| EVOC37 | 4 | | 4 | | | | 4 | | | | |
| EVOC38 | 4 | | 3 | | | | 3 | | | | |
| EVOC39 | 1 | | 1 | | | | 2 | | | | |
| EVOC40 | 4 | | 1 | | | | 2 | | | | |
| EVOC41 | 4 | | 2 | | | | | | | | |
| EVOC43 | 4 | | 4 | | | | 4 | | | | |
| EVOC44 | 4 | | 3 | | | | 4 | | | | |
| EVOC45 | 3 | | 3 | | | | 2 | | | | |
| EVOC46 | 3 | | 2 | | | | 1 | | | | |
| EVOC47 | 3 | | | | | | 3 | | | | |

0-Complete response; 1-strong partial response; 2-medium partial response; 3-weak partial response; and 4-No response.

The Developed EVOC can Predict Sensitivity to Targeted Therapy as Predicted by Molecular Profiling:

As a mean for personalized medicine, tumor tissue of the patient can be tested for possible actionable genetic mutations by e.g. exome sequencing. One of the tumors obtained was from a patient with a triple negative breast cancer that was found to harbor somatic genetic changes that are potentially targetable, including an amplification of FGFR1 and an amplification of CDK6. As can be seen in FIG. 7, while the tumor obtained from this patient (Patient 1) was resistant ex-vivo to the CDK4/6 inhibitor palbociclib it demonstrated high sensitivity to the FGFR inhibitor AZD4547. Most importantly, a breast cancer obtained from another patient that had no FGFR1 amplification (Patient 2) was resistant to FGFR inhibition in the developed EVOC system.

The tissue can be stored for 48 hours prior to culturing: Patient tumor tissues excised from patient tumors during surgical excision were directly cultured as described in the Materials and Methods and Example 1 hereinabove or cultured following 48 hours storage in medium at 4° C.; and the sensitivity of the tissue slices to anti-cancer agents was tested. FIG. 10 demonstrates an example for a colon cancer tissue that was found to be partially sensitive to 5-fluorouracil in a similar manner in both conditions (i.e. directly cultured or following 48 hours at 4° C.).

Taken together, the tissue can be stored in medium for at least 48 hours prior to beginning of experimentation without any adverse effects on the tissue or drug sensitivity.

Taken together, the newly developed EVOC makes the process of studying human cancer tissue response fast, cost effective and universal to many cancer tissues. All tested cancerous tissues including ovarian, colorectal, lung, pancreas and breast tissue presented high viability following 4-7 days in culture.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Dancey, J. E., Bedard, P. L., Onetto, N. & Hudson, T. J. The genetic basis for cancer treatment decisions. *Cell* 148, 409-420 (2012).
2. Garraway, L. A. Genomics-driven oncology: framework for an emerging paradigm. *J. Clin. Oncol. Off. J. Am. Soc. Clin. Oncol.* 31, 1806-1814 (2013).
3. Crystal, A. S. et al. Patient-derived models of acquired resistance can identify effective drug combinations for cancer. *Science* 346, 1480-1486 (2014).
4. Liu, X. et al. ROCK inhibitor and feeder cells induce the conditional reprogramming of epithelial cells. *Am. J. Pathol.* 180, 599-607 (2012).
5. Daniel, V. C. et al. A primary xenograft model of small-cell lung cancer reveals irreversible changes in gene expression imposed by culture in vitro. *Cancer Res.* 69, 3364-3373 (2009).

6. Clevers, H. Modeling Development and Disease with Organoids. *Cell* 165, 1586-1597 (2016).
7. Hidalgo, M. et al. Patient-derived xenograft models: an emerging platform for translational cancer research. *Cancer Discov.* 4, 998-1013 (2014).
8. Straussman, R. et al. Tumour micro-environment elicits innate resistance to RAF inhibitors through HGF secretion. *Nature* 487, 500-504 (2012).
9. Olson, O. C. & Joyce, J. A. Microenvironment-mediated resistance to anticancer therapies. *Cell Res.* 23, 179-181 (2013).
10. Vaira, V. et al. Preclinical model of organotypic culture for pharmacodynamic profiling of human tumors. *Proc. Natl. Acad. Sci. U.S.A* 107, 8352-8356 (2010).
11. Vickers, A. E. M. & Fisher, R. L. Organ slices for the evaluation of human drug toxicity. *Chem. Biol. Interact.* 150, 87-96 (2004).
12. de Kanter, R., Monshouwer, M., Meijer, D. K. F. & Groothuis, G. M. M. Precision-cut organ slices as a tool to study toxicity and metabolism of xenobiotics with special reference to non-hepatic tissues. *Curr. Drug Metab.* 3, 39-59 (2002).
13. Stoff-Khalili, M. A. et al. Preclinical evaluation of transcriptional targeting strategies for carcinoma of the breast in a tissue slice model system. *Breast Cancer Res.* BCR 7, R1141-1152 (2005).
14. Merz, F. et al. Organotypic slice cultures of human glioblastoma reveal different susceptibilities to treatments. *Neuro-Oncol.* 15, 670-681 (2013).
15. Gerlach, M. M. et al. Slice cultures from head and neck squamous cell carcinoma: a novel test system for drug susceptibility and mechanisms of resistance. *Br. J. Cancer* 110, 479-488 (2014).
16. Meijer, A. et al. Nutlin-3 preferentially sensitises wild-type p53-expressing cancer cells to DR5-selective TRAIL over rhTRAIL. *Br. J. Cancer* 109, 2685-2695 (2013).
17. Grosso, S. H. G. et al. Breast cancer tissue slices as a model for evaluation of response to rapamycin. *Cell Tissue Res.* 352, 671-684 (2013).
18. Majumder, B. et al. Predicting clinical response to anticancer drugs using an ex vivo platform that captures tumour heterogeneity. *Nat. Commun.* 6, 6169 (2015).
19. Roife, D. et al. Ex Vivo Testing of Patient-Derived Xenografts Mirrors the Clinical Outcome of Patients with Pancreatic Ductal Adenocarcinoma. *Clin. Cancer Res.* Jun. 3, 2016; DOI: 10.1158/1078-0432.CCR-15-2936.
20. Maund, S L. et al. Optimization and comprehensive characterization of a faithful tissue culture model of the benign and malignant human prostate. *Lab. Invest.* 94, 208-221 (2014).
21. Siolas, D., Hannon, G. Patient Dervided Tumor Xengrafts: transforming clinical samples into mouse models. *Cancer Res.* 73: 5315-5319 (2013).
22. Vaira, V. et al. Preclinical model of organotypic culture for pharmacodynamic profiling of human tumors. *PNAS* 107, 8352-8356 (2010).
23. van der Kuip, H., et al. Short term culture of breast cancer tissues to study the activity of the anticancer drug taxol in an intact tumor environment. *BMC Cancer* 6, 86-90.
24. Salmon, E., et al. Matrix architecture defines the preferential localization and migration of T-cells into the stroma of human lung tumors. *J. Clin. Invest.* 122, 899-910 (2012).

What is claimed is:

1. A method of culturing a cancer tissue, the method comprising culturing a precision-cut cancer tissue slice on a tissue culture insert in culture medium under a highly oxygenated atmosphere containing about 80% oxygen; and agitating the culture in a rotation facilitating intermittent submersion of said cancer tissue slice in said culture medium, wherein the cancer tissue is not liver tissue.

2. The method of claim 1, further comprising adding a drug to said culture medium.

3. The method of claim 1, wherein said cancer tissue is ovarian, colorectal, lung, pancreas, gastric, gastro esophageal, or breast cancer tissue.

4. The method of claim 2, wherein said drug is 5-fluorouracil (5FU), oxaliplatin, irinotecan, cisplatin, 4-hydroperoxy cyclophosphamide, docetaxel, doxorubicin, navalbine, gemcitabine, gefitinib, tamoxifen, olaparib, cetuximab, trametinib, everolimus, or palbociclib.

5. The method of claim 1, wherein said cancer tissue slice is cultured for at least 4 days.

6. The method of claim 1, wherein said slice is one slice.

7. The method of claim 1, wherein said slice is in direct contact with said tissue culture insert.

8. The method of claim 1, wherein said tissue culture insert is a titanium grid insert.

9. The method of claim 1, wherein the highly oxygenated atmosphere contains 80% oxygen.

10. The method of claim 5, wherein at least 70% of the cells in the precision-cut cancer tissue slice maintain viability after 4 days in culture.

11. The method of claim 5, wherein at least 80% of the cells in the precision-cut cancer tissue slice maintain viability after 4 days in culture.

12. The method of claim 1, wherein the cancer tissue culture slice is cultured for at least 5 days.

13. The method of claim 12, wherein at least 70% of the cells in the precision-cut cancer tissue slice maintain viability after 5 days in culture.

14. The method of claim 12, wherein at least 80% of the cells in the precision-cut cancer tissue slice maintain viability after 5 days in culture.

15. The method of claim 1, wherein the cancer is a carcinoma, blastoma, sarcoma, or lymphoma.

16. The method of claim 1, wherein the precision-cut cancer tissue slice is 200-300 µm thick.

17. The method of claim 1, wherein the culture medium is DMEM/F12 culture medium.

18. The method of claim 1, wherein the rotation facilitating intermittent submersion of said cancer tissue slice in said culture medium is performed at an agitation frequency of 50-100 rotations per minute (rpm).

19. A method of culturing a cancer tissue, the method comprising culturing a precision-cut 200-300 µm slice of a cancer tissue for at least 4 days on a tissue culture insert in DMEM/F12 culture medium under a highly oxygenated atmosphere containing about 80% oxygen; and agitating the culture in a rotation facilitating intermittent submersion of said cancer tissue slice in said culture medium, wherein at least 80% of the cells in the precision-cut cancer tissue slice maintain viability after 4 days in culture, wherein the cancer tissue is not liver tissue.

20. The method of claim 1, wherein the slice of the cancer tissue is a slice of a cancer tissue biopsy.

21. The method of claim 19, wherein the slice of the cancer tissue is a slice of a cancer tissue biopsy.

\* \* \* \* \*